(12) United States Patent
Gill et al.

(10) Patent No.: US 11,311,617 B2
(45) Date of Patent: *Apr. 26, 2022

(54) METHODS AND DEVICES FOR THE TREATMENT OF FOOD ALLERGIES

(71) Applicant: Texas Tech University System, Lubbock, TX (US)

(72) Inventors: Harvinder Singh Gill, Lubbock, TX (US); Akhilesh Kumar Shakya, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/354,099

(22) Filed: Jun. 22, 2021

(65) Prior Publication Data

US 2021/0315990 A1    Oct. 14, 2021

Related U.S. Application Data

(63) Continuation of application No. 16/616,171, filed as application No. PCT/US2018/035399 on May 31, 2018.

(60) Provisional application No. 62/576,176, filed on Oct. 24, 2017, provisional application No. 62/512,884, filed on May 31, 2017.

(51) Int. Cl.
| | | |
|---|---|---|
| *A61K 39/35* | (2006.01) | |
| *A61P 37/02* | (2006.01) | |
| *A61K 9/00* | (2006.01) | |
| *A61K 39/39* | (2006.01) | |
| *A61M 37/00* | (2006.01) | |
| *A61P 37/00* | (2006.01) | |
| *A61K 39/00* | (2006.01) | |

(52) U.S. Cl.
CPC ............ *A61K 39/35* (2013.01); *A61K 9/0021* (2013.01); *A61K 39/39* (2013.01); *A61M 37/0015* (2013.01); *A61P 37/00* (2018.01); *A61P 37/02* (2018.01); *A61K 2039/54* (2013.01); *A61K 2039/55561* (2013.01); *A61M 2037/0046* (2013.01); *A61M 2037/0061* (2013.01)

(58) Field of Classification Search
None
See application file for complete search history.

(56) References Cited

U.S. PATENT DOCUMENTS

| | | |
|---|---|---|
| 6,334,856 B1 | 1/2002 | Allen et al. |
| 6,611,707 B1 | 8/2003 | Prausnitz et al. |
| 6,743,211 B1 | 6/2004 | Prausnitz et al. |
| 9,730,987 B2 | 8/2017 | Detraz et al. |
| 2002/0082543 A1 | 6/2002 | Park et al. |
| 2004/0047902 A1 | 3/2004 | Dupont et al. |
| 2005/0209565 A1 | 9/2005 | Yuzhakov |
| 2006/0084942 A1 | 4/2006 | Kim et al. |
| 2006/0086689 A1 | 4/2006 | Raju |
| 2007/0161964 A1 | 7/2007 | Yuzhakov |
| 2010/0260821 A1 | 10/2010 | Dupont et al. |
| 2017/0202959 A1 | 7/2017 | Miller et al. |

FOREIGN PATENT DOCUMENTS

| | | |
|---|---|---|
| WO | 2013/033400 A2 | 3/2013 |
| WO | 2014/182932 A1 | 11/2014 |

OTHER PUBLICATIONS

Gill et al. 'Coated microneedles for transdermal delivery.' Journal of Controlled Release 117 (2007) 227-237.*
Blumchen et al. "Oral peanut immunotherapy in children with peanut anaphylaxis " J. Allergy Clin. Immunol. (2010), 126(1):83-91.
Commins et al. "Peanut Allergy: New Developments and Clinical Implications," Current Allergy and Asthma Reports (2016), 16(5):35.
Cox et al. "Allergen immunotherapy: A practice parameter third update." The Journal of allergy and clinical immunology (2011), 127(1 Suppl):S1-55.
De Leon et al. Immunological analysis of allergenic cross-reactivity between peanut and tree nuts, Clin. Exp. Allergy (2003), 33(9):1273-1280.
Deol and Bird, "Current opinion and review on peanut oil immunotherapy," Hum Vaccin. Immunother. (2014), 10 (10):3017-21.
Hofmann et al. "Safety of a peanut oral immunotherapy protocol in children with peanut allergy," J Allergy Clin Immunol. (2009), 124(2):286-291, 291.e1-6.
International Search Report and Written Oppinion for PCT/US2018/035399 [AU/RO] dated Aug. 1, 2018.

(Continued)

*Primary Examiner* — Nora M Rooney
(74) *Attorney, Agent, or Firm* — Edwin S. Flores; Daniel J. Chalker; Chalker Flores, LLP

(57) ABSTRACT

Methods and devices are provided for treating a food allergy in a subject in need thereof. The method entails delivering an effective amount of an allergen associated with the food allergy into the subject's cutis skin layer. Delivering the allergen is carried out by inserting one or more allergen-coated solid microneedles into the subject's skin. The one or more solid microneedles each has a base, shaft and tip, and when inserted in the subject, do not extend beyond the cutis. The allergen is allowed to dissociate from the one or more microneedles while inserted in the subject's cutis. Once the allergen disassociates, the one or more microneedles is removed from the subject's skin.

30 Claims, 11 Drawing Sheets

Specification includes a Sequence Listing.

(56) References Cited

OTHER PUBLICATIONS

Jain et al. "5-Aminolevulinic acid coated microneedles for photodynamic therapy of skin tumors," Journal of Controlled Release (2016), 239:72-81.
Jones et al. "Clinical efficacy and immune regulation with peanut oral immunotherapy," J Allergy Clin Immunol. (2009), 124(2):292-300.e97.
Jones et al. "Epicutaneous immunotherapy for the treatment of peanut allergy in children and young adults," J Allergy Clin Immunol. (2017), 139(4):1242-1252.
Karande and Mitragotri, "Transcutaneous Immunization: An Overview of Advantages, Disease Targets, Vaccines, and Delivery Technologies," Annu. Rev. Chem. Biomol. Eng. (2010), 1:175-201.
Li, et al., "A murine model of IgE-mediated cow's milk hypersensitivity," J Allergy Clin Immunol (1999), 103(2 Pt 1):206-14.
Ma et al. "Vaccine delivery to the oral cavity using coated microneedles induces systemic and mucosal immunity," Pharmaceutical Research (2014), 31(9:2393-2403.
McCaskill et al. "Anaphylaxis following intranasal challenge of mice sensitized with ovalbumin," Immunology (1984), 51(4):669-77.
Nelson et al. "Treatment of anaphylactic sensitivity to peanuts by immunotherapy with injections of aqueous peanut extract," J Allergy Clin Immunol. (1997), 99(6 Pt 1):744-51.
Oppenheimer et al. "Treatment of peanut allergy with rush immunotherapy," J Allergy Clin Immunol (1992), 90(2) 256-62.
Prausnitz et al. "Current Status and Future Potential of Transdermal Drug Delivery," Nat. Rev. Drug Discov. (2004), 3(2): 115-124.
Rosenfeld et al. "Walnut Allergy in Peanut-Allergic Patients: Significance of Sequential Epitopes of Walnut Homologous to Linear Epitopes of Ara h 1, 2 and 3 in Relation to Clinical Reactivity," Int. Arch. Allergy Immunol. (2012). 157(3):238-245.
Sampson, "Peanut Oral Immunotherapy: Is It Ready for Clinical Practice?" J Allergy Clin Immunol.: In Practice (2013), 1(1):15-21.
Sampson et al. "Food allergy: A practice parameter update—2014," J Allergy Clin Immunol. (2014), 134(5): 1016-1025 e43.
Shakya, A.K. et al., 'A comparative study of microneedle-based cutaneous immunization with other conventional routes to assess feasibility of microneedles for allergy immunotherapy', Vaccine. 2015, vol. 33, No. 33, pp. 4060-4064.
Shakya, A.K. et al., 'Cutaneous vaccination with coated microneedles prevents development of airway allergy', Journal of Controlled Release. Published online Aug. 15, 2017, vol. 265, pp. 75-82.
Sicherer et al. "Clinical Features of Acute Allergic Reactions to Peanut and Tree Nuts in Children," Pediatrics (1998), 102(1): e6.
Sicherer et al. "A voluntary registry for peanut and tree nut allergy: Characteristics of the first 5149 registrants," J Allergy Clin Immunol. (2001), 108(1):128-132.
Syed et al. "Peanut oral immunotherapy results in increased antigen-induced regulatory T-cell function and nypomethylation of forkhead box protein 3 (FOXP3)," J Allergy Clin Immunol. (2014), 133(2):500-510.e11.
Tang et al. "Surface Free Energy Changes of Stainless Steel after One Atmospheric Pressure Plasma Treatment," Korean J. Chem. Eng. (2004), 21(6):1218-1223.
Toebak et al. "Dendritic cells: biology of the skin." Contact Dermatitis (2009), 60(1):2-20.
Vickery et al. "Sustained unresponsiveness to peanut in subjects who have completed peanut oral immunotherapy," J Allergy Clin Immunol. (2014), 133(2):468-475.e6.
Vickery et al. "Early oral immunotherapy in peanut-allergic preschool children is safe and highly effective," J Allergy Clin Immunol. (2017), 139(1 ):173-181 e8.
Wood, "Food allergen immunotherapy: Current status and prospects for the future," J Allergy Clin Immunol. (2016), 137(4):973-982.
Wood, "Oral Immunotherapy for Food Allergy," J Investig Allergol Clin Immunol, (2017), 27(3):151-159.
Zhou et al. "Peanut Allergy, Allergen Composition, and Methods of Reducing Allergenicity: A Review," International Journal of Food Science, vol. 2013, Article ID 909140.
Caubet, Jean-Christoph et al. "Current understanding of egg allergy" Pediatr Clin North Am. Apr. 1, 2011; 58(2): 427-443.
Denisov, Ilia G. et al. "Nanodiscs in Membrane Biochemistry and Biophysics" Chem Rev. Mar. 22, 2017; 117(6): 1669-4713.
Bashir, M.M. et al. "TNF—a production in the skin" Arch Dermatol Res (2009) 301:87-91.
Chen, X. et al. "Facilitation of transcutaneous drug delivery and vaccine immunization by a safe laser technology" J Control Release Apr. 10, 2012; 159(1): 43-51.
Chen, X. et al. "Micro-fractional epidermal powder delivery for improved skin vaccination" J Control Release Oct. 28, 2014; 192: 310-316.
Gill, H. et al. "Coating Formulations for Microneedles" Pharmaceutical Research, vol. 24, No. 7, Jul. 2007.
Gill, H. et al. "Effect of microneedle design on pain in human subjects" Clin J Pain. Sep. 2008; 24(7): 585-594.
Guilliams, M. et al. "Skin-draining lymph nodes contain dermis-derived CD103 dendritic cells that constitutively produce retinoic acid and induce Foxp3+ regulatory T cells" Blood, Mar. 11, 2010, vol. 115, No. 10.
Gupta, J. et al. "Kinetics of Skin Resealing After Insertion of Microneedles in Human Subjects" J Control Release.Sep. 5, 2011; 154(2): 148-155.
Hessenberger, Michael et al. "Transcutaneous delivery of CpG-adjuvanted allergen via laser-generated micropores" Vaccine 31 (2013) 3427-3434.
Ingrole, Rohan S.J. et al. "Microneedle Coating Methods: A Review with a Perspective" J Pharmacol Exp Ther 370:555-569, Sep. 2019.
Ito, Sayami et al. "Immunogenicity of Milk Protein-Containing Hydrophilic Gel Patch for Epicutaneous Immunotherapy for Milk Allergy" Pharm Res (2020) 37: 35.
Kashiwagi, Satashi "Laser adjuvant for vaccination" The FASEB Journal 2020: 34:3485-3500.
Kim, YC et al. "Microneedles for drug and vaccine delivery" Adv Drug Deliv Rev. Nov. 2012; 64(14): 1547-1568.
Korotchenko, E. et al. "Laser-facilitated epicutaneous immunotherapy with hypoallergenic beta-glucan heoglycoconjugates suppresses lung inflammation and avoids local side effects in a mouse model of allergic asthma" Allergy. 2021;76:210-222.
Kreuse, K. et al. "The role of interleukin-1 in allergy-related disorders" Curr Opin Allergy Clin Immunol 2012, 12:477-484.
Kumar, Amit et al. "Permeation of antigen protein-conjugated nanopartides and live bacteria through microneedle-Yeated mouse skin" International Journal of Nanomedicine 2011:6 1253-1264.
Kumar, M.N.K. et al. "Laser-Facilitated Epicutaneous Immunotherapy to IgE-Mediated Allergy" J Control Relase Aug. 10, 2016; 235: 82-90.
Machado, Y et al. "Synergistic effects of dendritic cell targeting and laser-microporation on enhancing epicutaneous skin vaccination efficacy" Journal of Controlled Release 266 (2017) 87-99.
McAllister, D. V. et al. "Microfabricated needles for transdermal delivery of macromolecules and nanopartides: Fabrication methods and transport studies" PNAS Nov. 25, 2003 vol. 100 No. 24 13755-13760.
Mizutani, H. "Human Keratinocytes Produce but do not Process ProHnterleukin-1 (IL-1) Beta:Different Strategies of IL-1 Production and Processing in Monocytes and Keratinocytes" J. Clin. Invest. vol. 87, Mar. 1991, 1066-1071.
Mondoulet et al. "Intact skin and not stripped skin is crucial for the safety and efficacy of peanut epicutaneous immunotherapy (EPIT) in mice" Clinical and Translational Allergy 2012, 2:22; 12 pages.
Prausnitz, M.R. et al. "Microneedles for Drug Delivery" Modified-Release Drug Delivery Technology. CRC Press, 2008. 323-338.
Preissig, Jason et al. "Current Laser Resurfacing Technologies: A Review that Delves Beneath the Surface" Seminars in Plastic Surgery, vol. 26 No. 3/2012 109-116.
Shakya, A. K. et al. "Assessment of Th1/Th2 bias of STING agonists coated on microneedles for possible use in skin allergenimmunotherapy" Mol Pharm. Nov. 5, 2018; 15(11): 5437-5443.
Shakya, A. K. et al. "Coated microneedle based cutaneous immunotherapy prevents Der p1 induced airway allergy in mice" J Allergy Clin Immunol. Dec. 2018; 142(6): 2007-2011.

(56) References Cited

OTHER PUBLICATIONS

Shakya, A. K. et al. "Microneedle-Mediated Allergen-Specific Immunotherapy for the Treatment of Airway Allergy in Mice" Mol. Pharmaceutics 2020, 17, 3033-3042.

Sicherer et al. "Peanut and soy allergy: a clinical and therapeutic dilemma," Allergy (2000), 55(6): 515-521.

Fay, S. S. et al. "Patterns of immunoglobulin G responses to egg and peanut allergens are distinct: ovalbumin-specific immunoglobulin responses are ubiquitous, but peanut-specific immunoglobulin responses are up-regulated in peanut allergy" Clinical and Experimental Allergy, 37, 1512-1518.

Van der Burg, N. et al. "A low inflammatory, Langerhans cell-targeted microprojection patch to deliver ovalbumin to the epidermis of mouse skin" Journal of Controlled Release, Mar. 27, 2019, 36 pages.

Vicente-Perez, E. et al. "Repeat application of microneedled does not alter skin appearance or barrier function and causes no measurable disturbance of serum biomarkers of infection, inflammation or immunity in mice in vivo" European Journal of Pharmaceutics and Biopharmaceutics 117 (2017) 400-407.

Weiss, Richard et al. "Transcutaneous vaccination via laser microporation" Journal of Controlled Release 162 (2012) 391-399.

* cited by examiner

METHODS AND DEVICES FOR THE TREATMENT OF FOOD ALLERGIES

CROSS-REFERENCE TO RELATED APPLICATIONS

This application is a continuation of U.S. patent application Ser. No. 16/616,171, filed on Nov. 22, 2019, which is the National Stage of International Application No. PCT/US2018/035399, filed on May 31, 2019, which claims priority to U.S. Provisional Patent Application Ser. No. 62/512,884 filed on May 31, 2017 and U.S. Provisional Patent Application Ser. No. 62/576,176 filed on Oct. 24, 2017. The contents of all applications are incorporated by reference herein in their entirety.

STATEMENT OF FEDERALLY FUNDED RESEARCH

This invention was made with government support under grant number 1R01AI121322-01 awarded by the National Institutes of Health. The government has certain rights in the invention.

TECHNICAL FIELD OF THE INVENTION

The present invention relates to methods, devices and composition for the treatment of food allergies.

INCORPORATION-BY-REFERENCE OF MATERIALS FILED ON COMPACT DISC

The present application includes a Sequence Listing, which has been submitted in ASCII format via EFS-Web and is hereby incorporated by reference in its entirety. Said ASCII copy, created on May 30, 2018, is named TECH2103WO_SeqList and is 6 kilobytes in size.

BACKGROUND OF THE INVENTION

Peanut allergy is a life-threatening condition. About 1% of the U.S. population (~3 million people) has peanut allergies, and there is no FDA-approved treatment. Strict avoidance, and a peanut-free diet is the only option available to manage peanut allergies, which imposes severe limitations on the lifestyle of the patient and their families. Patients are also advised to carry an epinephrine injection to mitigate anaphylaxis, which can occur due to accidental peanut exposure. Adherence to a peanut-free diet imposes severe limitations on the lifestyle of the patient and their families, and reduces their quality of living. Importantly, restricted food diets in children can lead to nutritional deficiencies, and as such, methods for the treatment of peanut allergies are of great interest.

Peanut allergy is associated with an abnormal immune response to peanut proteins and it is mediated by peanut specific IgE antibodies. Allergic reaction to peanut in food can produce diverse symptoms including skin rashes, gastrointestinal reactions such as pain and vomiting, and even a severe life-threatening anaphylactic reaction (Sampson et al. (2014 *J Allergy Clin Immunol.* 134(5), pp. 1016-1025 e43). Oral immune-therapy (OIT) for peanut allergies is relatively new and experimental, and it aims to modulate this aberrant IgE response. The first open-label trial for peanut OIT was published in 2009 (Hofmann et al. (2009). *J Allergy Clin Immunol.* 124(2), pp. 286-291, 291.e1-6; Jones et al. (2009). *J Allergy Clin Immunol.* 124(2), pp. 292-300.e97).

The published protocols for peanut OIT (and food OIT in general) typically involve oral delivery of peanut flour/protein or extract in: (i) a rapid/rush dose escalation phase lasting one day (peanut protein dose increased from about 100 μg to 50 mg), (ii) a gradual dose buildup phase lasting many months (peanut protein dose increased to hundreds and thousands of milligram), and (iii) maintenance phase lasting months to years (peanut protein dose maintained at several thousand milligram). (Wood (2016). *J Allergy Clin Immunol.* 137(4), pp. 973-982; Deol and Bird (2014). Hum Vaccin. Immunother. 10(10), pp. 3017-21; Sampson (2013). *J Allergy Clin Immunol.: In Practice* 1(1), pp. 15-21.

The end-point of most peanut OITs has been to reorient the abnormal immune response and to desensitize the patient to peanut (Deol and Bird (2014). *Hum Vaccin. Immunother.* 10(10), pp. 3017-21; Sampson (2013). *J Allergy Clin Immunol.: In Practice* 1(1), pp. 15-21; Commins et al. (2016). *Current Allergy and Asthma Reports* 16(5), p. 35; Wood (2017). *J Investig Allergol Clin Immunol*, p. 0). Desensitization means increasing the patient's threshold to peanut reactivity (i.e., the amount of peanut that can be safely tolerated by the patient). To maintain desensitization, the patient is required to continue ingesting peanuts at a maintenance dose at regular intervals. However, sustained unresponsiveness, i.e., the ability of the patient to be nonresponsive to peanut ingestion after completion of OIT without the need to be on a maintenance dose, is the desirable treatment endpoint. In 2011 the first data of sustained unresponsiveness was published, and it was shown that 50% of the subjects were unresponsive to peanut 4 weeks after OIT (Vickery et al. (2014). *J Allergy Clin Immunol.* 133(2), pp. 468-475.e6). In another study, it was found that 7/20 subjects were unresponsive 3 months after stopping OIT, and only 3 out of these 7 were unresponsive another 3 months later (i.e., 3/20 were unresponsive 6 months after stopping OIT) (Syed et al. (2014). *J Allergy Clin Immunol.* 133(2): pp. 500-510.e11).

Current peanut OIT protocols require daily ingestion of peanut, and the dose is continuously increased to thousands of milligrams of peanut protein. Adverse events such as abdominal pain, vomiting, upper respiratory reactions (sneezing and congestion), and skin rashes/hives are very common, especially during the initial rush dose escalation from micrograms to tens of milligram in a single day (Hofmann et al. (2009). *J Allergy Clin Immunol.* 124(2), pp. 286-91, 291.e1-6), and the dose buildup phase when the peanut dose is raised from tens to thousands of milligrams (Vickery et al. (2017). *J Allergy Clin Immunol.* 139(1), pp. 173-181 e8). In one study, a direct correlation was observed between asthma and peanut OIT, wherein it was found that asthmatic patients experienced respiratory adverse events (Hofmann et al. (2009). *J Allergy Clin Immunol* 124(2), pp. 286-91, 291.e1-6).

Allergy shots, which are subcutaneously delivered, have a proven track record to provide long term treatment for environmental allergens that cause respiratory symptoms such as allergic rhinitis, allergic conjunctivitis, allergic asthma, or insect allergy (including bee venom) (Cox et al. (2011). The Journal of allergy and clinical immunology 127(1 Suppl), pp. S1-55). Building on this success, peanut subcutaneous immunotherapy was attempted in 1990s (Oppenheimer et al. (1992). *J Allergy Clin Immunol* 90(2), pp. 256-62; Nelson et al. (1997). *J Allergy Clin Immunol.* 99(6 Pt 1), pp. 744-51). Patients underwent rush immunotherapy, whereby they received four injections per day of increasing doses of peanut extract for five consecutive days, and then received eight injections (1/week) of maintenance dose. This was a small clinical study, and in three of the six patients, 67-100% reduction in symptoms was seen when they were orally challenged with peanut (Nelson et al. (1997). *J Allergy Clin Immunol.* 99(6 Pt 1), pp. 744-51). However, the systemic reactions were high. During rush immunotherapy, 23% of the injections given to the patients led to a systemic reaction needing epinephrine injection, while during maintenance phase this reaction rate was 33%. Based in part on these high reaction rates, the studies were halted. Subcutaneous injections have not been attempted again.

To circumvent the high reaction rate seen when peanut allergen is injected subcutaneously, a skin patch containing peanut allergen (100, 250 or 500 kg) was developed (34-38). This patch has now also completed a clinical trial (Jones et al. (2017). J Allergy Clin Immunol. 139(4), pp. 1242-1252), for which the patch was applied to the skin continuously for 24 hr. After 24 hr., the patch was removed and a new patch was immediately placed on a different skin site. Thus, the patient received a skin patch continuously, every day for one year. Low reaction rates were seen, and mostly these were observed topically on the skin. None of the patients could successfully complete the oral food challenge of 1044 mg (Jones et al. (2016). Consortium of Food Allergy, i Epicutaneous immunotherapy for the treatment of peanut allergy in children and young adults. J Allergy Clin Immunol). In contrast, peanut oral immunotherapy, although associated with a higher number of adverse events, has allowed patients to successfully complete oral challenges with about 4000 mg peanut protein (Hofmann et al. (2009). *J. Allergy Clin. Immunol.* 124(2), pp. 286-91, 291.e1-6; Jones et al. (2009). *J. Allergy Clin. Immunol.* 124(2), pp. 292-300.e97; Blumchen et al. (2010). *J. Allergy Clin. Immunol.* 126(1), pp. 83-91).

Based on the results of these clinical studies, new treatment options for peanut and other food allergies would be beneficial and an advance in the field. The present invention addresses this and other needs.

SUMMARY OF THE INVENTION

In one aspect, the present invention is directed to a method for treating a food allergy in a subject in need thereof. In one embodiment, the method for treating the food allergy comprises delivering an effective amount of an allergen associated with the food allergy into the subject's cutis. The delivering step comprises inserting one or more solid microneedles each having a base, shaft and tip into the subject's cutis. At least one of the one or more solid microneedles is coated with allergen associated with the food allergy and the one or more microneedles do not extend beyond the cutis once inserted. The allergen is allowed to dissociate from the microneedles while inserted in the subject's cutis. Once the allergen dissociates, the one or more microneedles are removed from the subject's skin.

The subject in one embodiment is a human. In a further embodiment, the human subject is from about 2 to about 12 years old, e.g., from about 4 to about 12 years old or from about 4 to about 10 years old. In one embodiment, the one or more solid microneedles comprise a microneedle array of two or more solid microneedles, for example, from about 10 to about 100 solid microneedles.

In one embodiment of the method, the one or more solid microneedles extends from an adhesive substrate. In one embodiment, the one or more solid microneedles are stainless steel. In a further embodiment, the average length of the one or more solid microneedles is from about 100 µm to about 1000 µm, as measured from the base of the tip. In even a further embodiment, the average length of the one or more solid microneedles is from about 200 µm to about 900 µm.

The one or more solid microneedles used in the methods and devices provided herein, in one embodiment, comprises from about 10 to about 150 microneedles, for example, from about 10 to about 100 microneedles, from about 10 to about 80 microneedles, or from about 20 to about 70 microneedles.

The methods provided herein are not limited to the type of food allergy that is treatable. For example, in one embodiment, the food allergy is a groundnut, peanut, milk, egg, tree nut, seed, fish, shellfish, crustacean, cereal, legume allergy, or a combination thereof. In one embodiment, the food allergy is a peanut allergy. In embodiments where a peanut allergy is treated, the peanut allergen can comprise Ara h1, Ara h2, Ara h3, Ara h4, Ara h5, Ara h6, Ara h7, Ara h8, Ara h9, Ara h10, Ara h11, Ara h12, Ara h13, a peptide fragment thereof, or a combination thereof. In a further embodiment, the peanut allergen comprises Ara h1, Ara h2, Ara h6, a peptide fragment thereof, or a combination thereof. Additionally, where a peanut allergen is coated on the microneedle array, it can be provided as peanut protein extract, protein flour, or a combination thereof.

In one embodiment of the method, once inserted into the cutis, the tip(s) of the one or more microneedles do not extend beyond the epidermis skin layer. In another embodiment, once inserted into the cutis, the tip(s) of the one or more microneedles do not extend beyond the dermis skin layer.

As provided above, in one embodiment, a method for treating a food allergy is provided comprising in part, inserting one or more solid microneedles into the subject's cutis, wherein at least one microneedle of the one or more solid microneedles is coated with allergen associated with the food allergy, and the at least one coated microneedle of the array does not extend beyond the cutis once inserted. In a further embodiment, each microneedle of the one or more microneedles does not extend beyond the cutis once inserted. The allergen is allowed to dissociate from the at least one microneedle while inserted in the subject's cutis. In a further embodiment, at least about 40%, at least about 50%, at least about 60%, at least about 70%, at least about 80%, or at least about 90% of the allergen disassociates from the at least one microneedle while inserted in the subject's cutis. Disassociation of the allergen in one embodiment, is carried out for about 1 minute to about 10 minutes, for example from about 1 minute to about 6 minutes or from about 1 minute to about 5 minutes.

As provided above, in one embodiment, a subject is treated for food allergy via delivering an effective amount of an allergen associated with the food allergy into the subject's cutis. Delivering is carried out via inserting one or more solid microneedles into the subject's cutis, wherein the one or more solid microneedles each comprises a base, shaft and tip. At least one microneedle of the one or more solid microneedles is coated with allergen associated with the food allergy and the at least one coated microneedle of the array does not extend beyond the cutis once inserted. In a further embodiment, each microneedle of the one or more solid microneedles does not extend beyond the cutis once inserted. The allergen is allowed to dissociate from the at least one microneedle while inserted in the subject's cutis. Once the allergen dissociates, the one or more solid microneedles is removed from the subject's skin. This method in a further embodiment, is carried out serially, over time. For example, in one embodiment, the method is carried out once daily, twice daily, three times daily, every other day, twice a week, or once weekly. In a further embodiment, the delivering an effective amount of an allergen results in delivering substantially the same amount of allergen each time the method is carried out. In another embodiment, the delivering an effective amount of an allergen results in delivering an escalating dosage of the allergen at least once, at least twice, or at least three times.

In one embodiment of the method of treating food allergy, the treating results in desensitization to the allergen. For example, in one embodiment, desensitization is by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, about 70%, about 75%, at least about 80%, at least about 85%, or at least about 90% as compared to the subject prior to commencing the treatment, a subject receiving a placebo or a subject not receiving the treatment.

In one embodiment of the method of treating food allergy, the treating results in a decrease in the number of allergen specific IgE antibodies in the subject, as compared to the number secreted prior to the treating. In another embodiment, the treating results in an increase in the number of allergen specific IgG antibodies in the subject, as compared to the number secreted prior to the treating. In a further embodiment, the subject is human and the allergen specific IgG antibodies are allergen specific IgG4 antibodies. In another embodiment, the treating results in a decreased number of mast cells in the subject, as compared to the number secreted prior to the treating. In a further embodiment, the decreased number of mast cells is at the site of allergen exposure (e.g., the GI tract for food allergens) in the subject, as compared to the number secreted at the site prior to the method being carried out. In yet another embodiment, the treating results in a decreased number of basophils in the subject, as compared to the number secreted prior to the treating. In a further embodiment, the decreased number of basophils is at the site of allergen exposure (e.g., the GI tract for food allergens) in the subject, as compared to the number secreted at the site prior to the method being carried out. In even another embodiment, the treating results in an increased cytokine production in the subject, as compared to the number secreted prior to the treating. In a further embodiment, the cytokine is IL-10 or TGF-β. In yet another embodiment, the treating results in an increased number of T-regulatory cells in the subject, as compared to the number of T-regulatory cells prior to the treating.

In one embodiment of the method of treating food allergy provided herein, the treating results in an increase in the eliciting dose of the allergen, as compared to the eliciting dose prior to initiation of treatment. For example, in one embodiment, the increase in the eliciting dose of the allergen is an increase by 10%, by 20%, by 30%, by 40%, by 50%, by 60%, by 70%, by 80%, by 90%, by 100%, by 500%, by 1000%, by at least about 10%, by at least about 20%, by at least about 30%, by at least about 40%, by at least about 50%, by at least about 60%, by at least about 70%, by at least about 80%, by at least about 90%, by at least about 100%, by at least about 500% or by at least about 1000%.

In one embodiment of the method of treating food allergy provided herein, the treating results in a sustained unresponsiveness to the allergen. In a further embodiment, the sustained unresponsiveness lasts for about 1 month, about 2 months, about 3 months, about 4 months, about 5 months, about 6 months, about 7 months, about 8 months, about 9 months, about 10 months, about 11 months, about 12 months, at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 12 months after therapy has ended.

In yet another aspect of the invention, a device is provided for the treatment of a food allergy. The device comprises a microneedle array comprising a plurality of solid microneedles extending from a common substrate. Each microneedle of the plurality has a base, shaft and tip, and at least one microneedle of the array is coated with a food allergen. In a further embodiment, the substrate is adhesive on at least one side. The substrate in one embodiment, is rigid. However, in another embodiment, the substrate is flexible.

In one embodiment of the device, the average length of the microneedles in the array is from about 100 µm to about 1000 µm, as measured from the base of the tip of the microneedles. In a further embodiment, the average length of the microneedles in the array is from about 100 µm to about 900 µm, or from about 100 µm to about 800 µm, or from about 100 µm to about 700 µm, or from about 100 µm to about 600 µm, or from about 100 µm to about 500 µm.

The device in one embodiment, comprises a microneedle array comprising from about 20 to about 150 microneedles, for example, from about 20 to about 150 microneedles, from about 30 to about 100 microneedles, or from about 40 to about 100 microneedles.

The device in one embodiment, comprises solid microneedles coated with a groundnut, peanut, milk, egg, tree nut, seed, fish, shellfish, crustacean, cereal, legume allergen, or a combination thereof.

The device in one embodiment, comprises solid microneedles coated with a peanut allergen. In a further embodiment, the peanut allergen can comprise Ara h1, Ara h2, Ara h3, Ara h4, Ara h5, Ara h6, Ara h7, Ara h8, Ara h9, Ara h10, Ara h11, Ara h12, Ara h13, a peptide fragment thereof, or a combination thereof. In a further embodiment, the peanut allergen comprises Ara h1, Ara h2, Ara h6, a peptide fragment thereof, or a combination thereof. Additionally, where a peanut allergen is coated on the microneedle array, it can be provided as peanut protein extract or peanut flour or a combination thereof.

BRIEF DESCRIPTION OF THE FIGURES

For a more complete understanding of the features and advantages of the present invention, reference is now made to the detailed description of the invention along with the accompanying figures and in which:

FIG. 8 (right) is a graph of the anaphylactic score as a function of time in naïve and sensitized mouse groups after oral challenge with PE. An anaphylactic scoring system based on mouse activity was used to evaluate anaphylactic severity as described previously by Li and McCaskill (Li et al. (1999). *J Allergy Clin Immunol* 103(2 Pt 1), pp. 206-14; McCaskill et al. (1984). *Immunology* 51(4), pp. 669-77, the disclosure of each of which is hereby incorporated by reference in its entirety for all purposes). 0: No symptoms; 1: Hypersensitivity to touch, irritation/aggression; 2: Puffiness around the eyes, pilar erection, reduced activity with increase respiratory rate; 3: Cyanosis around the mouth and tail, labored breathing, lying flat; 4: Loss of consciousness, no activity upon prodding, tremor or convulsions; 5: Death. All data illustrated as mean±SEM. *$p<0.05$, $p<0.01$, *$p<0.001$, and ****$p<0.0001$.

FIG. 9 (right) is a graph showing histamine release (concentration in plasma pg/mL) in naïve and sensitized mouse groups after oral challenge with PE. All data illustrated as mean±SEM. *$p<0.05$, **$p<0.01$.

FIG. 11 (top right) is a graph of anti-PE IgG1 antibodies, as measured by ELISA at different serum dilutions. FIG. 11 (bottom left) is a graph of anti-PE IgG2a antibodies, as measured by ELISA at different serum dilutions. FIG. 11 (bottom right) is a graph of anti-PE IgE antibodies, as measured by ELISA at different serum dilutions.

FIG. 17, top left: Post PE oral challenge, mice were monitored and their symptoms were scored and are shown as 'anaphylactic score'; 0: no symptoms; 1: hypersensitivity to touch, irritation/aggression; 2: puffiness around the eyes, pilar erection, reduced activity with increase respiratory rate; 3: cyanosis around the mouth and tail, labored breathing, lying flat; 4: loss of consciousness, no activity upon prodding, tremor or convulsions; 5: death. FIG. 17, top right: Anaphylaxis mediator histamine in plasma collected 5 minutes after challenge for the four mouse groups. FIG. 17, bottom left: Anaphylaxis mediator mast cell protease 1 (MCPT-1) in plasma collected 5 minutes after challenge for the four mouse groups. All data are illustrated as mean±SEM. *$p<0.05$, $p<0.01$, *$p<0.001$, and ****$p<0.0001$.

(FIG. 18, Left) anti-Ova IgG and (FIG. 18, Right) anti-Ova gG2a response in mice serum. Individual mouse serum was diluted to 1:100 and used in analysis. All data illustrated as mean±SEM. *$p<0.0005$, **$p<0.0001$ and ns; not significant. ELISA: Enzyme-linked immunosorbent assay.

(FIG. 19, Left) anti-Ova IgG, and (FIG. 19, Right) anti-Ova IgG2a response in mice serum. Individual mouse serum was diluted at 1:20 dilution and used in analysis. All data illustrated as mean±SEM. *$p<0.0005$, **$p<0.0001$ and ns; not significant. ELISA: Enzyme-linked immunosorbent assay.

(FIG. 20, Left) anti-PE IgG, (FIG. 20, Middle) anti-PE IgG2a and (FIG. 20, Right) anti-PE IgE response in mouse serum. Individual mouse serum was used in analysis. All data illustrated as mean±SEM. *$p<0.05$, **$p<0.005$ and ns; not significant.

FIG. 22, Left: 'Anaphylactic score'; 0: no symptoms; 1: hypersensitivity to touch, irritation/aggression; 2: puffiness around the eyes, pilar erection, reduced activity with increase respiratory rate; 3: cyanosis around the mouth and tail, labored breathing, lying flat; 4: loss of consciousness, no activity upon prodding, tremor or convulsions; 5: death. FIG. 22, Middle: Histamine level in serum. FIG. 22, Right: MCPT-1 level in serum. All data illustrated as mean±SEM. ****$p<0.0001$ and ns; not significant.

FIG. 23 (right) is a stereomicroscope fluorescent and brightfield mixed-light image of the same array. Scale bar for both images is 500 µm

DETAILED DESCRIPTION OF THE INVENTION

Figure 1:
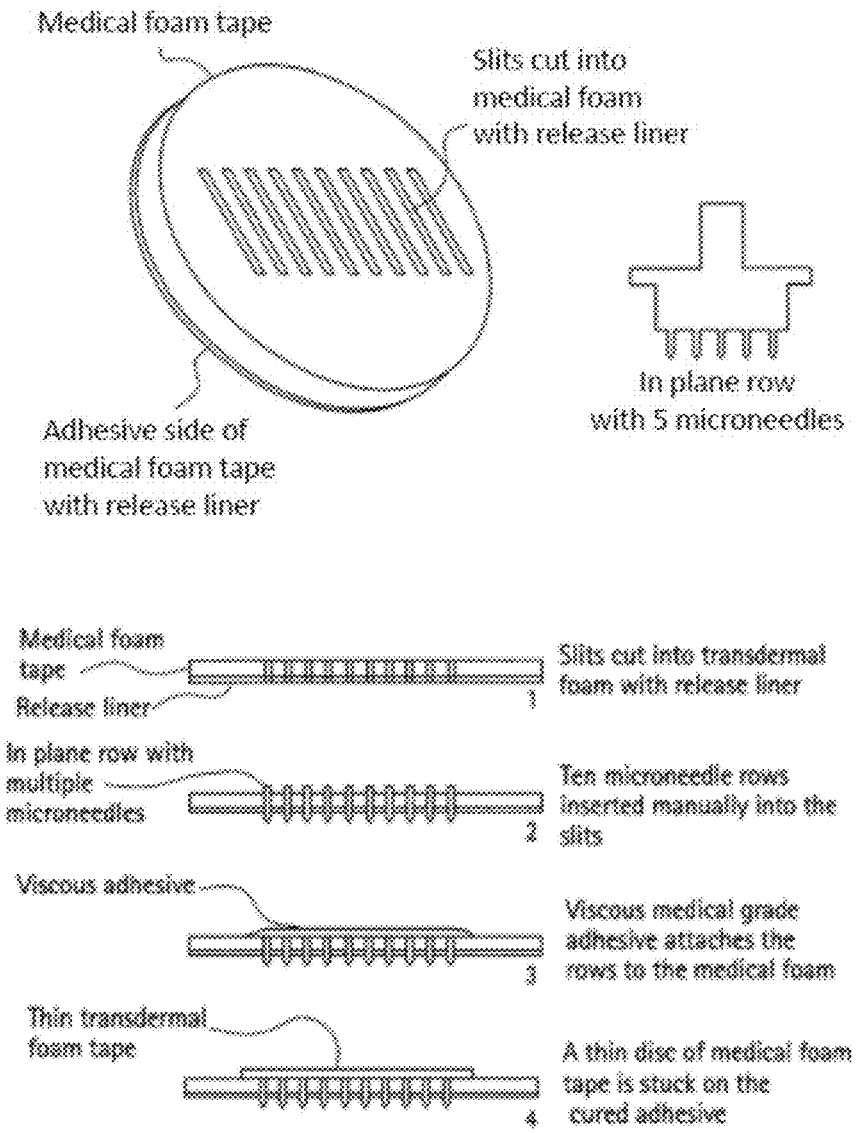
FIG. 1 illustrates one embodiment of a process for assembling a microneedle patch including coated in-plane microneedle rows as described herein.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Peanut allergy is a life-threatening condition. About 1% of the US population (~3 million people) has peanut allergies, and there is no FDA-approved treatment. As such, strict avoidance, i.e., a peanut-free diet, is the only option available to manage peanut allergies. Moreover, although oral immunotherapy, classical allergy shots and transdermal patches have all been attempted for the treatment of peanut allergy, each has drawbacks such as the lack of sustained unresponsiveness, and the presence of adverse events.

Specifically, a major limitation of oral immunotherapy is that the peanut oral dose is escalated to thousands of milligrams, which can cause various side effects. Additionally, peanut oral immunotherapy has only been shown in some instances to offer short term desensitization. Moreover, allergy shots, when administered for peanut allergy, resulted in systemic reactions after rush immunotherapy. Transdermal patches, currently being developed, are also met with challenges. Appreciating that skin is impermeable to large molecules such as proteins (see, e.g., Karande and Mitragotri (2010). *Annu. Rev. Chem. Biomol. Eng.* 1, pp. 175-201; Prausnitz et al. (2004). *Nat. Rev. Drug Discov.* 3(2), pp. 115-124, the disclosure of each of which is incorporated by reference in its entirety for all purposes), the delivery of peanut proteins from such a skin patch is in all likelihood very low, and as such, it is not surprising that the immune modulating effect is not that strong. Indeed, none of the patients is the transdermal patch study could successfully complete the oral food challenge of 1044 mg (Jones et al. (2017). *J Allergy Clin Immunol.* 139(4), pp. 1242-1252, the disclosure of which is incorporated by reference in its entirety for all purposes).

The present invention addresses the need in the art for a new treatment method for food allergy, and specifically, peanut allergy by providing microneedle arrays for the application to a patient's skin. Microneedles (MNs) are sharp microstructures, and due to their small size, MNs can be non-invasive and painless. Due to their micrometer dimensions, coated MNs also have the potential to allow targeting of the allergens to dendritic cells, e.g., Langerhans cells (LCs) that reside in the topmost hundred micrometers of the skin epidermis.

Skin dendritic cells (DCs) play a central role in the initiation of allergic skin responses. Following encounter with an allergen, DCs become activated and undergo maturation and differentiate into immunostimulatory DCs and are able to present antigens effectively to T cells. (Toebak et al. (2009). *Contact Dermatitis* 60(1), pp. 2-20, incorporated by reference herein in its entirety for all purposes). Without wishing to be bound by theory, it is thought that because MNs can target dendritic cells, e.g., LCs in the skin, they can help in dose reduction of the respective food antigen, e.g., peanut antigen.

In one aspect, the present invention is directed to a method for treating a food allergy in a subject in need thereof. In one embodiment, the method for treating the food allergy comprises delivering an effective amount of an allergen associated with the food allergy into the subject's cutis. The delivering step comprises inserting a one or more microneedles (e.g., present as a microneedle array) into the subject's cutis, wherein the one or more microneedles each has abase, shaft and tip. At least one microneedle of the one or more microneedles is coated with allergen associated with the food allergy and the at least one coated microneedle of the array does not extend beyond the cutis once inserted into the subject's skin. However, in some embodiments described herein, each microneedle of the array does not extend beyond the cutis once inserted. In a further embodiment, substantially all the microneedles are coated with the allergen. The allergen is allowed to dissociate from the one or more microneedles while inserted in the subject's cutis. Once the allergen dissociates, the one or more microneedles is removed from the subject's skin.

In one embodiment, the microneedle tips of the one or more microneedles extend into the epidermis layer of the subject's skin once inserted. In a further embodiment, the microneedle tips extend into the epidermis layer of the skin and do not extend into the dermis layer once inserted into the subject. However, in some embodiments, the microneedle tips do extend into the dermis layer. It should be noted that unlike a subcutaneous injection, the microneedles provided herein do not extend beyond the dermis layer of the skin, i.e., the microneedles do not extend into the subcutis. Additionally, microneedles of the one or more microneedles can be fabricated having different lengths. As a result, different microneedles can extend to different depths in the cutis.

The one or more microneedles can be present as an array of two or more microneedles, i.e., as a microneedle array. The one or more microneedles (e.g., microneedle array) comprises at least one solid microneedle coated with or associated with one or more food allergens that are specific to the food allergy. In one embodiment, substantially all of the microneedles in the array are coated with the one or more food allergens. In another embodiment, a majority of the microneedles in the array are coated with the one or more food allergens.

Because microneedles are very small structures, they are painless. In embodiments of the treatment methods provided herein, a microneedle array is inserted into the subject's skin one or more times for a time sufficient to cause a protective immune response, e.g., desensitization or sustained unresponsiveness to the allergen. The allergen dose can be the same or different for each insertion/application. For example, microneedle arrays can be applied serially, and deliver an escalating dose of the allergen, or combinations of allergens.

The one or more microneedles (e.g., microneedle array) in one embodiment is inserted into a subject's skin one or more times for about 1 min. to 1 hr., for example, from about 1 min. to about 10 min., or from about 1 min. to about 5 min for each insertion (also referred to as an application). Where the one or more microneedles is inserted into a subject's skin multiple times (i.e., multiple applications), in one embodiment, there is an "off period" in between the multiple applications/insertions. The "off period" in one embodiment, is 12 hrs., one day, two days, three days, four days, five days, six days, seven days or 14 days. As such, the one or more microneedles (e.g., the microneedle array) can be applied at various frequencies until desensitization and/or sustained unresponsiveness to the allergen is achieved. In one embodiment, the one or more microneedles (e.g., microneedle array) is inserted into a subject's skin once daily, twice daily, every other day, every third day, or once a week until a protective immune response is achieved. The time sufficient to achieve desensitization and/or long term unresponsiveness is 1 month, 3 months, 6 months, 12 months, 18 months, 24 months 30 months or 36 months.

As used herein, the term "subject" is used to mean an animal, for example a mammal, including a human or non-human. The terms subject and patient can be used interchangeably. The subject can be a child or an adult. In one embodiment, a subject is from about 2 to about 30 years old. In a further embodiment, the subject is human. In another embodiment, the subject is human and is from about 2 years old to about 12 years old. In a further embodiment, the subject is a human subject and is from about 4 years old to about 11 years old or about 4 years old to about 10 years old.

As used herein, the term "treating" or "treatment" refers to the ability to achieve desensitization to the respective allergen, and/or long term unresponsiveness (also referred to as sustained unresponsiveness). In one embodiment, the desensitization is characterized relative to the same subject, prior to commencing therapy, or compared to a subject receiving placebo or not receiving treatment. In one embodiment, the subject is desensitized by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, about 70%, about 75%, at least about 80%, at least about 85%, or at least about 90% as compared to the subject prior to commencing therapy, a subject receiving a placebo or a subject not receiving treatment.

An "effective amount" of an allergen is an amount of allergen that can provide desensitization to the allergen, and/or the increase in eliciting dose of the allergen. The effective amount can be delivered in a single treatment step, or as part of a treatment regimen where multiple doses are given during the treatment regimen. The treatment regimen can include substantially the same dose for each allergen administration, or can comprise at least one, at least two or at least three escalating dosages.

Successful desensitization can be characterized in one embodiment, by a decrease in the number of allergen specific IgE antibodies, and/or increased production of T regulatory cells. The T-regulatory cells in one embodiment, are Tr1 cells (produce IL-10, IL-10+), (ii) Th3 cells (produce TGF-β, latency associated peptide:LAP+), (iii) CD4+ CD25+forkhead box P3:Foxp3+ Tregs, or a combination thereof.

In another embodiment, successful desensitization is characterized by an increase in cytokine production (e.g., IL-10, TGF-β), increased production of IgG allergen specific antibodies (e.g., IgG4 in humans, IgG2a in mice), decreased number of mast cells (e.g., at the site of allergen exposure (e.g., the gastrointestinal tract (GI) in the case of food allergens) as compared to prior to treatment), decreased number of basophils (e.g., at the site of allergen exposure (e.g., the gastrointestinal tract (GI) in the case of food allergens), or a combination of the foregoing.

Successful treatment can also be measured by an increase in the eliciting dose of the allergen, as compared to the eliciting dose prior to initiation of treatment. The "eliciting dose" of an allergen or allergenic food, as used herein, is the lowest dose of allergen or allergenic food containing the allergen, that causes a response in a subject that is sensitized to the allergen, e.g., symptoms of an allergic reaction. "Eliciting dose" can also be used interchangeably with "threshold dose". The symptoms can be skin inflammation/redness, upper airway (eyes, nose, and throat), lower airway (lungs), gastrointestinal, cardiovascular and/or neurological symptoms, as assessed by one of ordinary skill in the art. In one embodiment, the symptom is a mild, objective symptom in a sensitized subject, e.g., a highly sensitized subject. See, e.g., Taylor et al. (2004). *Clin Exp. Allergy* 34, pp. 689-695, the disclosure of which is incorporated herein in its entirety for all purposes.

Low dose challenges can begin, e.g., at 10 µg of the allergen and can continue to increase based on the judgement of one of ordinary skill in the art. In one embodiment, a 30 minute or 1 hr. interval is used between doses. In one embodiment, the dose increase is an increase in an order of magnitude.

In one embodiment, a peanut allergen challenge comprises the administration of a peanut flour to a subject. The peanut flour can be defatted, and can comprise Florunner, Virginia, or Spanish peanut flour, or a combination thereof. In one embodiment, the peanut flour comprises equal parts Florunner, Virginia and Spanish peanut flour. In another embodiment, roasted peanuts are used as the challenge material. The foregoing compositions can also be used to coat the microneedles provided herein.

"Long term unresponsiveness" and "sustained unresponsiveness" are used interchangeably herein, and refers to the lack of clinical reactivity to the ingested food allergen for 1 month to 1 year after therapy has ended. In one embodiment, the sustained unresponsiveness lasts for about 1 month, about 2 months, about 3 months, about 4 months, about 5 months, about 6 months, about 7 months, about 8 months, about 9 months, about 10 months, about 11 months or about 12 months after therapy has ended. In one embodiment, the sustained unresponsiveness lasts for at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 12 months after therapy has ended.

In one embodiment, the food allergy is a milk, fish, shellfish or nut allergy. In one embodiment, the food allergy is a nut allergy. In a further embodiment, the nut allergy is a soy or a peanut allergy. In even a further embodiment, the nut allergy is a food allergy.

The one or microneedles (e.g., present as a microneedle array) provided herein can be used to delivery one or more food allergens to a subject in need thereof in order to desensitize the subject to the allergen, and/or to obtain a sustained unresponsiveness to the allergen.

The term "allergen" refers to an immunogenic molecule (or a combination thereof) involved in an allergic reaction contained in food. The allergen in one embodiment, is a lipid, carbohydrate, protein, peptide, polypeptide, or a combination thereof. In one embodiment, the allergen is a native food preparation, a food extract, or a purified protein, polypeptide and/or peptide composition. The allergen may be in a natural state, or produced artificially (e.g., by recombinant and/or enzymatic techniques, and or de novo synthesis for instance). The allergen in one embodiment, is structurally altered or modified to improve its stability or immunogenicity. The allergen in on embodiment is in admixture with one or more other constituents, such as an adjuvant. The allergen may be a mixture of several molecules (e.g., an extract such as a peanut protein extract). The allergen may be present in combination with other allergens, or in combination with other molecules from the food that are not immunogenic. In one embodiment, one or more adjuvants are included in a composition comprising the allergen.

The invention may be used with any food or food allergens such as, without limitation, groundnut, peanut, milk, egg, tree nuts and seeds (such as but not limited to: hazelnut, cashew, walnut, pecan, brazil nut, macadamia, chestnut, pistachio, coconut, almond, sesame, mustard), fish, shellfish, crustaceans, cereals (e.g., wheat, corn, oat, barley, rye, rice, sorghum, spelt), legumes (e.g., soy, kidney bean, black bean, common bean, chickpea, pea, cow pea, lentils, lupine), or mixtures thereof.

In one embodiment, the allergen is a peanut allergen or a combination of peanut allergens. The peanut allergen in one embodiment is in the form of a peanut protein extract. Thirteen peanut allergens (Ara h1 through Ara h13) have been recognized by the Allergen Nomenclature Sub-Committee of the International Union of Immunological Societies (Zhou et al. (2013). *International Journal of Food Science*, V. 2013, Article ID 909140, incorporated by reference herein in its entirety). In one embodiment, the peanut allergen comprises one or more of Ara h1, Ara h2, Ara h3, Ara h4, Ara h5, Ara h6, Ara h7, Ara h8, Ara h9, Ara h10, Ara h11, Ara h12 or Ara h13, or a peptide fragment of one of the foregoing, or a combination thereof. In a further embodiment, the peanut allergen comprises Ara h1, Ara h2, Ara h3, a peptide fragment thereof, or a combination thereof. In yet another embodiment, the peanut allergen comprises Ara h1, a peptide fragment thereof, or multiple peptide fragments thereof.

Peanut Flour (PF) for use as an allergen composition can be obtained commercially, for example, from the Golden Peanut Company (Alpharetta, Ga.). The PF can be defatted, and can comprise in one embodiment, Florunner, Virginia, or Spanish PF, or a combination thereof. In one embodiment, the peanut flour comprises equal parts Florunner, Virginia and Spanish PF. In another embodiment, roasted peanuts are used as a source of allergen for the allergen composition. Peanut extract for use as an allergen composition in another embodiment, can be obtained commercially, for example, from Greer Labs (Lenoir, N.C.).

In one embodiment, the peanut allergen comprises Ara h1 (or a peptide fragment thereof), Ara h2 (or a peptide fragment thereof), and Ara h6 (or a peptide fragment thereof).

Representative linear epitopes for peanut allergens are provided in Zhou et al. (Zhou et al. (2013). *International Journal of Food Science*, V. 2013, Article ID 909140, incorporated by reference herein in its entirety). For example, for Ara h1, epitope sequences that can be incorporated into the peanut allergen include PGQFEDFF (epitope #7), YLQGFSRN (epitope #8), FNAEFNEIRR (epitope #9), QEERGQRR (epitope #10), DITNPINLRE (epitope #11), NNFGKLFEVK (epitope #12), GNLELV (epitope #13), RRYTARLKEG (epitope #14), ELHLLGFGIN (epitope #15), HRIFLAGDKD (epitope #16), IDQIEKQAKD (epitope #17), KDLAFPGSGE (epitope #18), KESHFVSARP (epitope #19), NEGVIVKV-SKEHVEELTKHAKSVSK (epitope #21), or a combination thereof.

Peptides that may be incorporated into an Ara h2 peanut allergen include HASARQQWEL (epitope #1), QWELQGDRRC (epitope #2), DRRCQSQLER (epitope #3), LRPCEQHLMQ (epitope #4), KIQR.DEDSYE (epitope #5), YERDPYSPSQ (epitope #6), SQDPYSPSPY (epitope #7), DRLQ..GRQQEQ (epitope #8), KRELRNLPQQ (epitope #9), QRCDLDVESG (epitope #10), or a combination thereof.

Peptides that may be incorporated into an Ara h3 allergen include IETWNPNNQEFECAG (epitope #1), GNIFSGFT-PEFLAQA (epitope #2), VTVRGGLRILSPDRK (epitope #3), DEDEYEYDE-EDRRRG (epitope #4), or a combination thereof.

In one embodiment, the allergen is a legume allergen or a tree nut allergen. For example, the allergen in one embodiment is soy. In another embodiment, the allergen is almond, pecan, hazelnut, walnut or a combination thereof. It should be noted that certain patients are sensitized against more than one type of food allergen (Sicherer et al. (1998). *Pediatrics* 102(1), p. e6; Sicherer et al. (2001). *J Allergy Clin Immunol.* 108(1), pp. 128-132, each of which is incorporated by reference herein in its entirety for all purposes). As such, some embodiments of the invention are directed to the delivery of multiple allergens to a patient in the treatment methods provided herein. Alternatively, an allergen is cross reactive to two different food substances, and therefore, in one embodiment, a cross reactive allergen can be used to desensitize a patient to multiple food allergens. In cross-reactivity, IgE antibodies against one allergen can bind to a different homologous allergen and trigger the adverse reaction similar to that elicited by its binding to the first allergen. Homologous allergens share structural similarity or common epitopes, which increases the chances of cross-reactivity. For example, peanut proteins share structural homology within the legume family (e.g. soy protein), and with certain tree nuts (e.g. almond, pecan, hazelnut, and walnut) (Sicherer et al. (2000). *Allergy* 55(6), pp. 515-521; de Leon et al. (2003). Clin. Exp. Allergy 33(9), pp. 1273-1280; Rosenfeld et al. (2012). *Int. Arch. Allergy Immunol.* 157(3), pp. 238-245, each of which is incorporated by reference herein in its entirety for all purposes).

The one or more allergens provided herein are delivered to a subject in need thereof in an allergen composition. The allergen composition includes at least one allergen in a pharmaceutically acceptable vehicle. In one embodiment, the allergen composition further comprises one or more adjuvants.

An "adjuvant" is substance added to one of the allergens provided herein to increase the allergen's immunogenicity, as compared with its immunogenicity in absence of the adjuvant. An adjuvant may be included in an allergen composition provided herein, for example, to increase the efficacy of the allergen and/or to induce or enhance an immune response that is not sufficiently induced in the absence of the adjuvant. In some embodiments, the adjuvant enables a lower dose of the allergen. In another embodiment, the adjuvant enables a more rapid immune response. The practical result of the more rapid immune response is a reduction in a multi-dosing regimen to a fewer number of doses, and in some cases, a single dose.

The adjuvant can be mixed with the allergen and present in the same microneedle coating. Alternatively, the adjuvant and allergen can be coated on separate microneedles. In one embodiment where an adjuvant is delivered with an allergen with a microneedle array, the allergen and adjuvant are coated on different microneedles of a microneedle array. In a further embodiment, individual rows of a microneedle array are coated with either the allergen or the adjuvant. See, e.g., FIG. 23 left and right.

Figure 23:
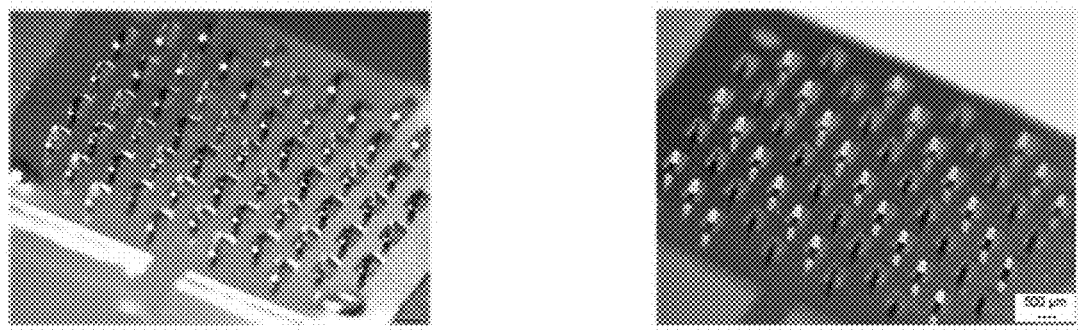
FIG. 23 (left) is a stereomicroscope brightfield image of a microneedle array whose alternate diagonal rows are coated with two different dyes (green fluorescent fluorescein isothiocyanate and red fluorescent sulforhodamine) to simulate an allergen and an adjuvant coating on separate rows of microneedles.

FIG. 23 (left) is a stereomicroscope brightfield image of a microneedle array whose alternate diagonal rows are coated with two different dyes (green fluorescent fluorescein isothiocyanate and red fluorescent sulforhodamine) to simulate an allergen and an adjuvant coating on separate rows of microneedles: FIG. 23 (right) is a stereomicroscope fluorescent and brightfield mixed-light image of the same array. Scale bar for both images is 500 µm.

In one embodiment, the adjuvant is an aluminum salt, inulin, L-Tyrosine, algammulin, combination of inulin and aluminum hydroxide, monophosphoryl lipid A (MPL), L-Tyrosine in combination with MPL, resiquimod, muramyl dipeptide (MDP), N-glycolyl dipeptide (GMDP), poly IC, CpG oligonucleotide, resiquimod, aluminum hydroxide with MPL, any water in oil emulsion, any oil in water emulsion that contains one or more of the following constituents: squalene or its analogues or any pharmaceutically acceptable oil, tween-80, sorbitan trioleate, alpha-tocopherol, cholecalciferol, calcium phosphate or a combination of two or more of the foregoing.

In one embodiment of the allergen composition provided herein, the composition comprises a stimulator of interferon genes (STING) ligand adjuvant. The STING ligand in one embodiment, is a cyclic dinucleotide or a xanthenone derivative. In a further embodiment, the STING ligand is cyclic guanosine monophosphate (cGMP), cyclic di-GMP (c-diGMP), cyclic adenosine monophosphate (cAMP), cyclic-di-AMP (c-di-AMP), cyclic-GMP-AMP (cGAMP, e.g., 2'2'-cGAMP, 2'3'-cGAMP or 3'3'-cGAMP). STING ligands are available commercially, e.g., from Invivogen (San Diego, Calif., USA).

In another embodiment, the adjuvant is an oil and water emulsion (for example, complete Freund's adjuvant and incomplete Freund's adjuvant, *Corynebacterium parvum*, *Bacillus* Calmette Guerin, aluminum hydroxide, glucan, dextran sulfate, iron oxide, sodium alginate, Bacto-Adjuvant, certain synthetic polymers such as poly amino acids and co-polymers of amino acids, saponin, Avridine (N, N-dioctadecyl-N',N'-bis(2-hydroxyethyl)-propanediamine), paraffin oil, muramyl dipeptide or a combination thereof.

In one embodiment, the allergen composition comprises alum as an adjuvant.

In one embodiment, the adjuvant in the allergen composition is L-Tyrosine. Various animal studies have shown L-Tyrosine to be a safe and effective adjuvant, with high adsorptive power for proteins, and enhancement of antibody indication as well as a short-term depot. See, e.g., Baldrick et al. (2002). J. Appl. Toxicol. 22, pp. 333-344, the disclosure of which is incorporated by reference herein in its entirety for all purposes.

In another embodiment, the adjuvant in the allergen composition is monophoshoryl lipid A (MPL).

In another embodiment, the adjuvant in the allergen composition is L-Tyrosine in combination with monophoshoryl lipid A (MPL).

In one embodiment, the adjuvant in the allergen composition is a CpG oligonucleotide (ODN). For example, the CpG adjuvant is one or more adjuvants disclosed in U.S. Patent Application Publication No. 2017/0136119, the disclosure of which is incorporated by reference in its entirety for all purposes.

In yet another embodiment, the allergen is delivered with an adjuvant selected from alum; a CpG oligonucleotides (ODN); polyA-polyU; dimethyldioctadecylammonium bromide (DDA), N,N-dioctadecyl-N',N'-bis(2-hydroxyethyl) propanediamine, carbomer, chitosan (see, e.g., U.S. Pat. No. 5,980,912 for example, the disclosure of which is incorporated herein by reference in its entirety for all purposes.

The adjuvant, in another embodiment, comprises a lipophile, a polymer of acrylic or methacrylic acid, saline, cholesterol, a saponin, sodium hydroxide, or a combination thereof. For example, one or more of the adjuvants disclosed in U.S. Patent Application Publication No. 2017/0202959 and U.S. Pat. No. 9,730,987, the disclosure of each of which is incorporated herein by reference in its entirety for all purposes.

The devices and methods provided herein employ one or more microneedles to deliver an allergen into a subject's cutis. In one embodiment, a single microneedle is employed. However, in another embodiment, two or more microneedles are employed. The two or more microneedles can be in the form of a microneedle array. A microneedle patch in embodiments described herein, includes one or more microneedles extending from a common substrate. Where two or more microneedles are employed, e.g., as an array, each microneedle need not be coated with allergen. However, in one embodiment, substantially every microneedle is coated with allergen.

"Microneedle array" as used herein, refers to two or more microneedles extending from a common substrate. Each microneedle includes a base, a tip portion and a shaft between the base and tip portion. The two or more microneedles in the array need not be homogenous with respect to size, shape and/or material. In other words, a microneedle array may include a mixture of different microneedles. For example, an array may include microneedles having various lengths, base portion diameters, tip portion shapes, spacings between microneedles, drug coatings, etc. However, in one embodiment, the two or more microneedles in the array are substantially the same size and shape, and are fabricated from the same material. In a further embodiment, the two or more microneedles in an array are each fabricated from stainless steel, and are solid microneedles. In one embodiment, the microneedle comprises between 2 and 1000 (e.g., between 2 and 500) microneedles. In one embodiment, the microneedle array comprises between 2 and 250 microneedles, for example, between 2 and 100 microneedles, or from 10 to 100 microneedles.

The microneedles provided herein can be fabricated of different biocompatible materials, including metals, glasses, semi-conductor materials, ceramics, or polymers. Examples of suitable metals include pharmaceutical grade stainless steel, gold, titanium, nickel, iron, tin, chromium, copper, alloys thereof, and combinations thereof. In one embodiment, microneedles are fabricated from stainless steel.

In another embodiment, the microneedle is fabricated from a polymer substrate. The polymer can be biodegradable or non-biodegradable. Examples of suitable biocompatible, biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Representative non-biodegradable polymers include polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. Biodegradable microneedles can provide an increased level of safety compared to non-biodegradable ones, such that they are essentially harmless even if inadvertently broken off into the biological tissue. In embodiments where biocompatible polymers are employed, the allergen can either be coated on the surface of the microneedle, or encapsulated with the polymer for example, as described in PCT Publication WO 2014/182932, the disclosure of which is incorporated by reference herein in its entirety. For example, a solution of biocompatible polymer can be mixed with allergen and cast in a mold to form microneedles.

The microneedles employed herein can be solid or hollow. In addition, the microneedles can be porous or non-porous. The microneedles may be planar, cylindrical, or conical. The microneedles can have a straight or tapered shaft. In one embodiment, the microneedle array comprises two or more solid microneedles. In a further embodiment, each microneedle in the array is a solid microneedle.

In one embodiment, the diameter of one or more of the microneedles in the array is greatest at the base end of the microneedle (i.e., the portion attached to the substrate) and tapers to a point at the end distal the base. In a further embodiment, each of the microneedles in the array has a diameter that is greatest at the base, which tapers to a point at the end distal to the base. The microneedles can also be fabricated to have a shaft that includes both a straight (i.e., untapered) portion and a tapered portion. In another embodiment, one or more microneedles in the array are straight, while one or more microneedles are tapered. In yet another embodiment, the microneedles in the array comprise shafts that have a circular cross-section in the perpendicular. However, in another embodiment, the microneedles in the array comprise shafts that have a non-circular cross-section.

Each microneedle employed herein includes a tip portion. The tip portion can have a variety of configurations. The tip portion can be symmetrical or asymmetrical about the longitudinal axis of the shaft. Moreover, the tip portion in one embodiment, is beveled, tapered, squared-off, or rounded. The tip portion, in one embodiment, has a length that is less than 50% of the total length of the microneedle.

Microneedle length selection, as an initial matter, is selected considering whether the entire length of the microneedles is inserted, or whether a portion of the microneedles is inserted with a portion that remains uninserted. The length of a microneedle is measured from the base, i.e., the portion of the microneedle attached to the substrate, to the tip of the microneedle. In the case of a microneedle array, where two or more microneedles are employed, the microneedles can have substantially the same length, or different lengths. Different lengths can be employed, for example, to deliver allergen to different depths in the subject's cutis. In one embodiment, the average length of the microneedles in a microneedle array is from about 50 µm to about 5000 µm, from about 100 µm to about 1500 µm, from about 200 µm to about 1000 µm, from about 200 µm to about 800 µm, from about 200 µm to about 700 µm. In one embodiment, the average length of the microneedles in the array is from about 500 µm to about 1000 µm. In yet another embodiment, the average length of the microneedles in the array is about 150 µm, about 250 µm, about 300 µm, about 500 µm, about 600 µm, about 700 µm, about 750 µm, about 800 µm or about 850 µm.

The cross-section of the microneedle, or width, is tailored to provide, among other things, the mechanical strength to remain intact for the delivery of the drug or for serving as a conduit (i.e., in the case of a hollow microneedle), while being inserted into the skin, while remaining in place during its functional period, and while being removed (unless designed to break off, dissolve, or otherwise not be removed). In various embodiments, the base portions of the microneedles in the array have an average width or cross-sectional dimension from about 20 µm to about 500 µm, for example from about 50 µm to about 350 µm, or from about 100 µm to about 250 µm. In one embodiment, the width of the microneedles in the array is substantially the same in the base and the shaft of the microneedles.

The one or more microneedles, in one embodiment, have an average aspect ratio (width:length) of from about 1:1 and 1:10. The tip of the microneedle can sharpen gradually as in the case of microneedles with a conical, pyramidal, or triangular cross-section. In another embodiment the tip can be suddenly formed into a sharp point as in the case of microneedles with cylindrical cross-section. In one embodiment, the microneedles have an aspect ratio of about 1:3.5 with a cross-section that is rectangular for about 70% of its length followed by a tapering triangular shape constituting the remaining about 30% of the top, and culminating in to a sharp tip.

The one or more microneedles, in one embodiment, includes a microneedle comprising a pocket. As used herein, "pocket" refers to an aperture extending crosswise into the microneedle shaft (e.g., perpendicular to the direction of microneedle movement during the process of insertion into skin). The pocket can extend through the shaft. However, the pocket in another embodiment, is closed at one end, distal the opening in the shaft. This is distinct from a hollow bore wherein a concentric space extends substantially through the axial length of the shaft. The pockets are considered to be part of the surface of the microneedle. In one embodiment, the pocket is included in a solid microneedle, and includes coating material which may be particularly advantageous in certain embodiments where the coating material needs to be protected from mechanical forces during the insertion process, e.g., when the coating comprises a liquid or particles. Without wishing to be bound by theory, it is thought that such coating materials are more likely than others to be prematurely dislodged from the microneedle during insertion into skin, diminishing the complete delivery of the complete dosage of the coating. However, the pockets of the microneedles advantageously function to shield the coating material therein from the mechanical forces of insertion. The pockets may be made in various shapes (e.g., circular, square, rectangular) and of various numbers and dimensions and different spacings within the microneedle.

The microneedles in the arrays provided herein can be fabricated by a variety of methods known in the art. In one embodiment, a wet etch process is employed. For example, the wet etch processes described in Ma et al. (2014). *Pharmaceutical Research* 31(9), pp. 2393-2403; Jain et al. (2016). *Journal of Controlled Release* 239, pp. 72-81, each of which is incorporated by reference herein in its entirety for all purposes, can be employed.

Details of other contemplated manufacturing techniques are described, for example, in U.S. Patent Application Publication No. 2006/0086689, U.S. Patent Application Publication No. 2006/0084942, U.S. Patent Application Publication No. 2005/0209565, U.S. Patent Application Publication No. 2002/0082543, U.S. Pat. Nos. 6,334,856, 6,611,707, 6,743,211, each of which is incorporated herein by reference in its entirety for all purposes.

In one embodiment, the microneedles are cut from stainless steel or other metal sheets using a laser (e.g., an infrared laser) or other techniques known in the art.

In one embodiment, an electropolishing technique is used to produce clean, smooth, and sharp solid microneedles. Electropolishing can remove slag deposits from the microneedles, as laser-cutting of metals such as stainless steel may produce microneedles with rough edges covered with slag deposits. In one embodiment, laser cut stainless steel microneedles are electropolished in a solution that includes glycerin, ortho-phosphoric acid (85%), and water. In one example, a copper plate is used as the cathode and the metal microneedles serve as the anode. The anode may be vibrated using means known in the art to help remove gas bubbles generated at the anodic surface during electropolishing. Electropolishing is believed to be especially effective, because current density (i.e., etching rate) is largest at sites of high curvature, which inherently targets sites of surface roughness for removal. In some embodiments, the electropolishing process has an output rate of finished microneedle arrays of one 50-needle array every 30 minutes using a single laser. This rate can be increased by process optimization and use of multiple lasers.

In one embodiment, the microneedle array used in the methods provided herein (or the single microneedle) includes a substantially planar foundation from which two or more microneedles extend (or the single microneedle extends), typically in a direction normal (i.e., perpendicular or out-of-plane) to the foundation. Alternatively, microneedles may be fabricated on the edge of a substrate 'in-plane' with the substrate. In one embodiment, the microneedle array extends from a flexible base substrate. In another embodiment, the microneedle array extends from a curved base substrate. The curvature of the base substrate typically would be designed to conform to the shape of the tissue surface. The curved base substrate can be flexible or rigid.

In one embodiment, the one or more microneedles extends from an adhesive patch substrate. The patch comprises one or more microneedles, for example, an array of tens or hundreds of microneedles (e.g., from about 10 to about 500 microneedles or from about 10 to about 100 microneedles). The patch, in one embodiment, comprises an adhesive component to secure the patch to the skin. The patch includes a plurality of linear rows of in-plane microneedles, a plurality of individual arrays of out-of-plane microneedles, or a combination thereof.

The patch, e.g., adhesive patch, can be a flexible or rigid substrate which includes a pressure sensitive adhesive as known in the art.

In one embodiment, the microneedles and adhesive component are configured such that the microneedles extend through apertures in the adhesive layer. Individual microneedles or subgroups of microneedles (e.g., rows) can extend through a single aperture. Without wishing to be bound by theory, it is thought that when the adhesive surface is adjacent the microneedles, the adhesive is able to better hold the microneedles down and to compensate for the recoiling-tendency of skin and/or a rigid substrate for out-of-plane microneedles.

In one embodiment, in-plane microneedles are fabricated with a uniform adhesive layer in between the microneedles. For example, rows of microneedles can be assembled into a patch by forming slits (equal to the length of an in-plane row) in a material, e.g., polyethylene medical foam tape. Such cutting can be performed by any suitable technique known in the art, such as laser cutting. The microneedle rows can be manually or robotically inserted into each slit from the non-adhesive side of the foam tape and glued to the foam tape using a medical grade adhesive. The adhesive is then allowed to cure. Optionally, a medical foam tape of sufficient thickness can then be cut into a disc and affixed onto the dried glue area to provide a cushioned backing to facilitate pressing the patch during insertion. See FIG. 1. In one embodiment, the thickness of the medical foam tape is from about 0.4 mm to about 1.0 mm, or from about 0.6 mm to about 1.0 mm, or from about 0.7 mm to about 0.9 mm, e.g., 0.8 mm.

In another embodiment, a microneedle patch is assembled using out-of plane microneedles, a circular disc of a single-sided medical foam tape and a thick double-sided medical tape. In the middle of the disc, a rectangular piece of adhesive release liner equal in dimensions to the periphery of the array can be cut out and peeled off. The microneedle array can then be attached to this exposed adhesive. To provide a layer of pressure-sensitive adhesive on the stainless steel substrate of the affixed array itself, a double-sided, carrier tape first perforated with holes corresponding to the microneedles can be attached by slipping it over the microneedles using an alignment device. In one embodiment, the carrier tape is a polyethylene terephthalate (PET) carrier tape.

In one embodiment, microneedle array patches are assembled into transdermal patches containing pressure-sensitive adhesive to adhere to the skin. To secure microneedles in the skin at all times until ready to be removed, microneedles in one embodiment, are integrated into a Band-Aid-like patch. The patch had pressure-sensitive adhesive on one complete side, with microneedles protruding therefrom. The adhesive secured the microneedles and compensated for the recoiling tendency of the skin and the rigid stainless steel material of the out-of-plane microneedles (i.e., microneedles normal to the patch substrate). Patches can be fabricated using either multiple linear rows of in-plane microneedles or individual arrays of out-of-plane microneedles.

In-plane microneedles, in one embodiment, are fabricated with a uniform adhesive layer in between the microneedles. In this embodiment, a set of rows of microneedles (e.g., 10 rows), each containing, for example, 5-10 microneedles each, can be assembled into a patch of, for example, 50-100 microneedles. In one embodiment, slits are laser cut into a single sided medical foam tape. Each slit is cut to the length of a row of microneedles, and the number of slits corresponds to the number of microneedle rows in the patch. Microneedle rows can be manually or robotically inserted into each slit from the non-adhesive side of the foam tape, and glued to the foam tape using a medical grade adhesive. The adhesive can then be allowed to cure for a sufficient amount of time, for example from about 12 hours to about 48 hours, for example about 24 hours. A medical foam tape can then be cut to size of the assembled array, and affixed onto the dried glue area to provide a cushioned backing to facilitate pressing the patch during insertion.

In one embodiment, a microneedle patch is assembled with out-of plane microneedles. In this embodiment, a circular disc of appropriate diameter is cut from a single-sided medical foam tape, for example, using a $CO_2$ laser. One of ordinary skill in the art will appreciate that the diameter of the disk will be dictated by the size and shape (e.g., number of rows) of the microneedle array. In the middle of this disc, a rectangular piece of the adhesive release liner equal in dimensions to the periphery of the array can be cut out, e.g., using a $CO_2$ laser, and subsequently peeled off. The stainless steel microneedle array can then be attached to this exposed adhesive. To provide a layer of pressure-sensitive adhesive on the stainless steel substrate of the affixed array itself, a double-sided carrier tape (e.g., polyethylene terephthalate (PET) tape) can be attached. The carrier film is first perforated with holes at the same spacing as the microneedles using a $CO_2$ laser. The tape is then slipped over the microneedles using a custom-built alignment device and pressed to stick against the stainless steel microneedles.

The coated solid microneedles provided herein can be fabricated via methods known to those of ordinary skilled in the art. For example, in one embodiment, the coated microneedles are fabricated via the methods disclosed in U.S. Pat. No. 9,364,426, the disclosure of which is incorporated by reference in its entirety for all purposes.

In one embodiment, prior to coating the microneedle or microneedles with allergen, the microneedle or microneedles are treated with oxygen or air plasma. Such treatment has been reported to increase the surface energy and wettability of certain substrates such as stainless steel. See, e.g., Tang et al. (2004). *Korean J. Chem. Eng.* 21(6), pp. 1218-1223, the disclosure of which is incorporated by reference in its entirety for all purposes. Moreover, an oxygen or air plasma treatment may result in additives not being needed in the subsequent allergen coating (e.g., additive to facilitate coating adhesion), and can serve to sterilize the microneedle surface.

In some embodiment, prior to coating the one or more microneedles (e.g., microneedle array) with the allergen or combination of allergens, a precoating to at least one surface of the microneedles is performed, in order to increase the surface energy of the surface, or to otherwise modify the surface energy properties of the microneedles. In another embodiment, the coating liquid is modified to decrease the surface tension of the coating liquid. A combination of the aforementioned can also be carried out. It should also be noted that a precoating need not be applied to all microneedles of the one or more microneedles. Nor does the coating liquid need to be modified for all microneedles, when a modification of the coating liquid is performed.

The coating liquid in one embodiment, is disposed in one or more reservoirs. Microneedles can be dipped directly into the reservoir containing the allergen or combination of allergens. In another embodiment, a physical mask having a plurality of apertures therethrough, each aperture having cross-sectional dimensions larger than the at least one microneedle to be coated is provided over the reservoir. In this embodiment, the microneedle array is aligned with the plurality of apertures, and the array is inserted through the aligned aperture and into the coating liquid. The coated microneedle array is then removed from the coating liquid and from the apertures. The one or more reservoirs may be defined in a secondary structure or the physical may have a plurality of the reservoirs defined therein.

By utilization of a physical mask, access of the coating liquid is restricted only to the microneedle shaft and tip, thereby preventing contamination of the substrate from which the microneedles extend. Thus, any meniscus rise or capillary action that may cause contact of the coating liquid to an adjacent microneedle or with the substrate is avoided such that the coating is on the surface of the microneedle shafts and tips, and the base substrate is free of the coating.

In one embodiment, the physical mask is in the form of a plate having a one or more discrete apertures therethrough. The apertures, in one embodiment, are in the form of one or more holes or slits which closely circumscribe each microneedle, a single row of microneedles, multiple rows of microneedles, or another subset of microneedles of the array. As used herein, the term "closely circumscribe" means that the physical mask is effective to restrain, for example, by surface tension forces, the coating liquid to the reservoir and apertures, preventing it from "climbing up" the microneedle shaft substantially beyond the dipped portion of the microneedle which it is desired to coat. Surface energy properties of the coating system (physical mask, microneedle, and coating fluid) and operating conditions (e.g., temperature, dipping/withdrawal speed) can impact the selection of appropriate dimensions for the holes and slits.

Figure 2:
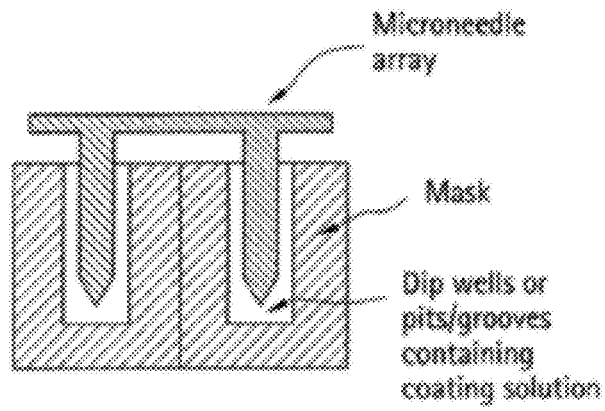
FIG. 2 is a cross sectional view of microneedles in a microneedle array which are dipped into an allergen coating liquid using a physical mask to control deposition of coating, with the mask having multiple dip holes built into the mask.

In one embodiment, the physical mask is in the form of a substantially rigid plate secured to the reservoir (see, e.g., FIG. 2). The plate includes an array of micron-sized holes which are used for inserting the microneedles to be coated. When aligned, for example using micropositioners or pre-aligned parts moving on a rail, each of the microneedles can be simultaneously inserted through the micron sized holes and into the coating liquid, resulting in a controlled micro-dip-coating process. The use of one or more micropositioners can be used to provide control over the microneedle length being coated, that is how much of the microneedle length is actually coated. In one embodiment, physical stops in the form of thick sheets or protruding cylinders in between the physical mask and microneedles, or a combination thereof, are used to control the microneedle length being coated. The coating device can be configured to coat single microneedles, in-plane rows of microneedles, and out-of-plane arrays of microneedles.

Figure 3:
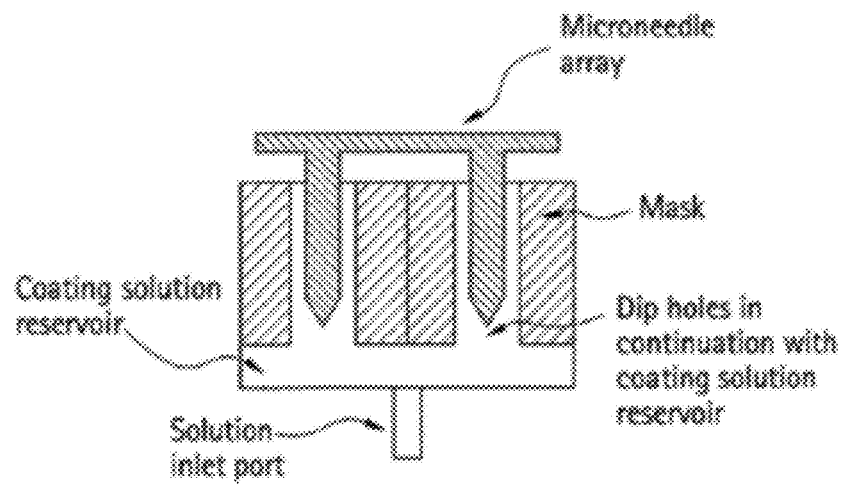
FIG. 3 is a cross sectional view of microneedles in a microneedle array which are dipped into an allergen coating liquid using a physical mask to control deposition of coating, with a single reservoir in fluid communication with open dip holes.

In another embodiment, the physical mask acts as a coating liquid reservoir or reservoirs. For example, in one embodiment, the physical mask includes reservoirs, closed at one end, that can be filled with the coating liquid (see, e.g., FIG. 3). Single microneedles or multiple microneedles of an array can be dipped into each reservoir. In one embodiment, the apertures of the mask have a closed bottom, and the coating liquid is filled in these apertures from the open top. However, an inlet port can be present on the bottom of the apertures to fill coating liquid. Apertures can be periodically or continually refilled to maintain a constant amount of coating liquid in the reservoir(s).

To reduce propensity of air bubbles in the reservoir and/or apertures in the plate, vent holes designed to release entrapped air can be provided in the coating apparatus. To prevent evaporation of coating liquid (or solvent thereof)

from the coating liquid, a pumping device (e.g., an automated or manually pulsated syringe plunger) can be included with the coating apparatus to fill the coating liquid reservoir and to oscillate/mix the coating liquid in dip-coating holes. The coating liquid in the reservoir may be flowed or agitated to facilitate maintenance of a uniform coating liquid composition during the dipping process. Alternatively, or additionally, the coating process may be performed at a reduced temperature (relative to ambient) to reduce the rate of evaporation of the coating liquid or solvent portion thereof.

In one embodiment, the coating process includes the step of volatilizing at least a portion of the solvent to form a solid coating. This may be referred to as "drying" the coating or coating liquid. A similar step may be included when using molten coating liquids, wherein the coated liquid is permitted to (or actively caused to) cool the molten material sufficiently to cause it to solidify, forming a solid coating on at least a portion of the microneedles of the array.

Microneedles can be coated with a single coating or multiple coatings. For example, the coating method in one embodiment includes inserting at least one coated microneedle of a coated microneedle array into the same or a different coating liquid and then removing the microneedle from said same or different coating liquid. The composition of the coating liquid may include a solvent to dissolve part of the previous coating, if desired. In another embodiment, the coating method includes the step of applying a second coating liquid onto the solid coating or onto a second surface of the microneedle in need of coating. The composition of the second coating liquid may include a second antigenic epitope. Multiple such dippings into the same or a different coating liquid may be repeated.

The coating process can also include an optional intervening dip into a cleaning solvent, e.g., to thin or remove part of a coating layer. This may be useful to build complete coating structures, e.g., where one coating composition is located on one part of the microneedle (e.g., a first pocket) and a second coating composition is located on another part of the microneedle (e.g., a second pocket).

To obtain uniform coatings on microneedle surfaces, it is generally desired that the surface tension of the coating liquid is lower than the surface energy of the microneedle surface material (material of construction or overcoat deposition). A slow (taking more than a second) or rapid (taking less than a second, e.g., less than a tenth of a second or less than a hundredth of a second) withdrawal of the microneedle from the immersed state to outside the coating liquid will provide a uniform coating on the microneedle. Addition of a viscosity enhancer to the coating solution increases the coating thickness by increasing the film thickness of the entrained liquid during withdrawal. However, the requirement of coating liquid surface tension being lower than the microneedle material can be overcome by conducting the coating process at a rate faster than is needed to achieve thermodynamic equilibrium. For instance, by increasing the viscosity and withdrawing at a rapid speed, the microneedle will entrain a significant volume of the liquid on the surface. If the solvent then evaporates before the liquid film can contract to form an island in the middle of the microneedle surface, the solid coating will become uniformly deposited onto the microneedles. Another way to overcome the surface tension barrier to obtain uniform coatings is to use a non-aqueous solvent that has lower surface tension, possibly lower than the microneedle material. Similarly, while coating only the pockets, advantage can be made of the kinetic effect by utilizing a high surface energy liquid/solution that will not wet the microneedle surface but will fill the pockets. Again, the speed must be sufficiently slow so that liquid does not entrain on the surface, but only gets into the pockets.

EXAMPLES

The present invention is further illustrated by reference to the following Examples. However, it should be noted that these Examples, like the embodiments described above, are illustrative and are not to be construed as restricting the scope of the invention in any way.

Example 1—Intradermal Delivery of Model Antigen Via Coated Microneedles

Figure 4:
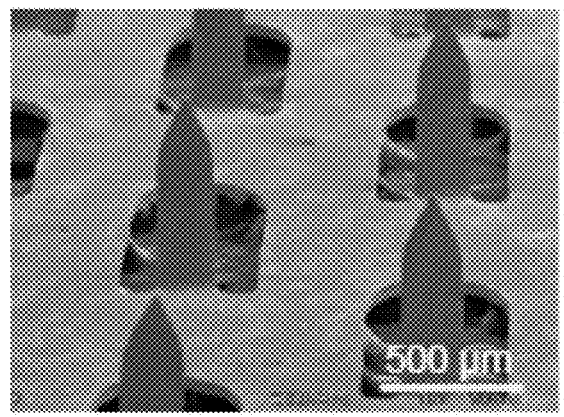
FIG. 4 is a scanning electron micrograph of one embodiment of a microneedle array.

Microneedle arrays were fabricated from 50 μm-thick stainless steel (304) sheets using a wet etch process. Each microneedle measured about 700 μm in length and about 200 μm in width, and each microneedle array contained 57 microneedles. Microneedle arrays were fabricated as described previously (see, e.g., Ma et al. (2014). *Pharmaceutical Research* 31(9), pp. 2393-2403; Jain et al. (2016). *Journal of Controlled Release* 239, pp. 72-81, each of which is incorporated by reference herein in its entirety for all purposes. The individual microneedles were then manually bent to make them perpendicular to the metal sheet (FIG. 4). Microneedles were coated using a micro-precision dip coating station developed in-house. It comprised of an automated x-y linear computer-controlled stage on to which microneedles were mounted. The coating solution was housed in an orifice in to which the microneedles were dipped through motion control of the x-y stage, as described by Ma et al. (Ma et al. (2014). *Pharmaceutical Research* 31(9), pp. 2393-2403, incorporated by reference in its entirety for all purposes).

Figure 5:
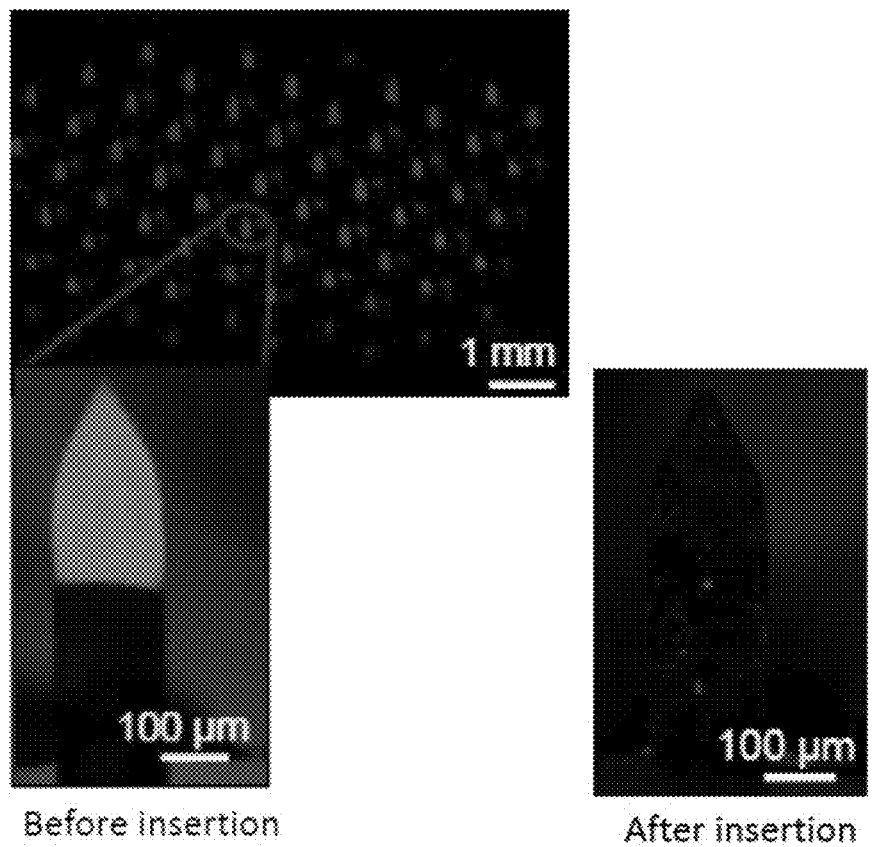
FIG. 5 is a fluorescent micrograph of a microneedle array prior to insertion into the skin. The insets are of a single microneedle prior to insertion (left) and after insertion (right).
Figure 6:
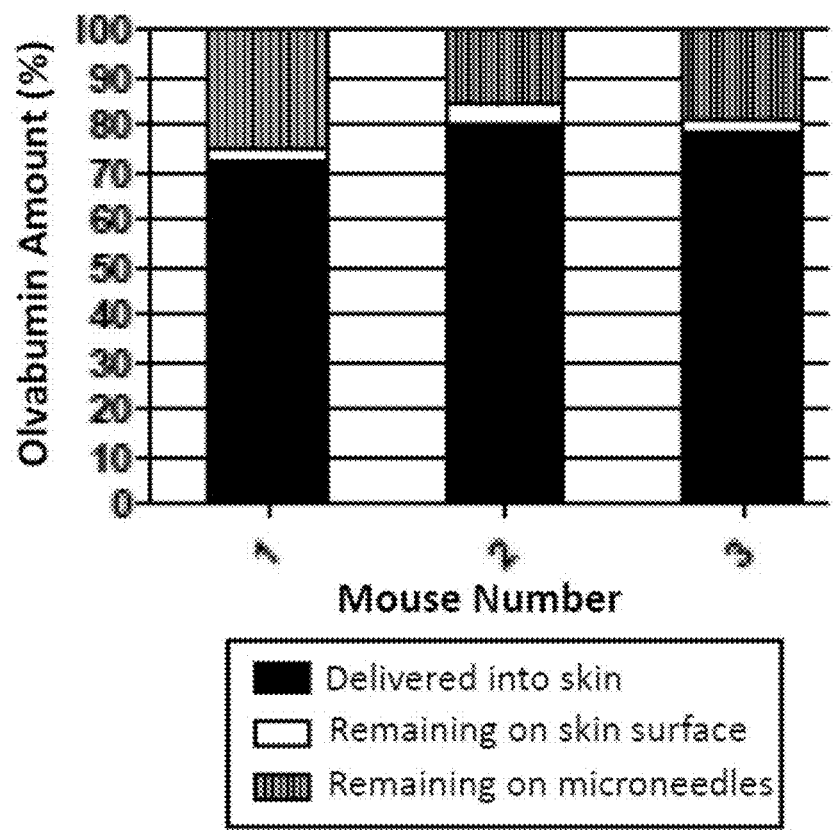
FIG. 6 is a bar graph showing the amount of ovalbumin (Ova) delivered into mouse skin via microneedles, as well as the amount of Ova remaining on microneedles and on the skin surface. Ova was quantified via fluorescein-conjugated Ova ($\lambda$ex437 nm/$\lambda$em515 nm) through spectrofluorometer.

The coating solution was composed of 1% (w/v) carboxymethylcellulose (CMC) sodium salt (low viscosity, USP grade, CarboMer, San Diego, Calif., USA), 0.5% (w/v) Lutrol F-68 NF (BASF, Mt. Olive, N.J., USA), and fluorescent OVA labeled with fluorescein as a model allergen. CMC and Lutrol F-68 are FDA approved for injection, and are thus safe excipients to use. Coated microneedle arrays were inserted in mouse skin for 5 min (FIG. 5). Mouse skin was first prepared by carefully trimming the hair and then by applying hair-removing lotion. The mass of OVA on fresh microneedle array (M1), on microneedle array after insertion (M2), and on skin surface (obtained by using a cotton tip and extracting in water) (M3) was quantified using fluorescent spectroscopy and a standard curve of fluorescein-OVA. The amount of OVA delivered into skin was then obtained (M1-M2-M3), and converted into percent delivered by dividing with M1. Greater than 70% of OVA coated on MNs was delivered into the mouse skin (FIG. 6).

Example 2—Mouse Model for Peanut Allergy

Figure 7:
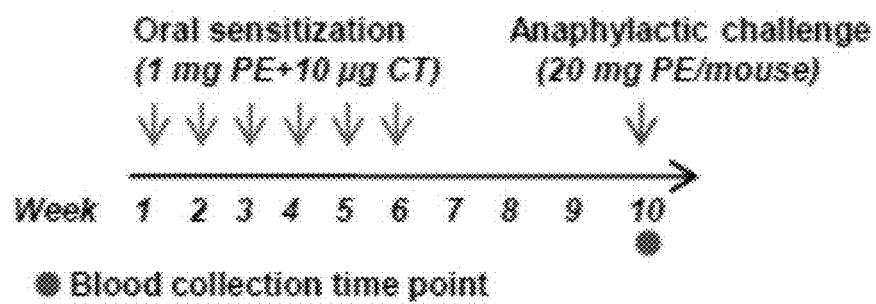
FIG. 7 shows the schedule and doses for sensitization and oral peanut challenge in Balb/c mice with peanut extract (PE).
Figure 8:
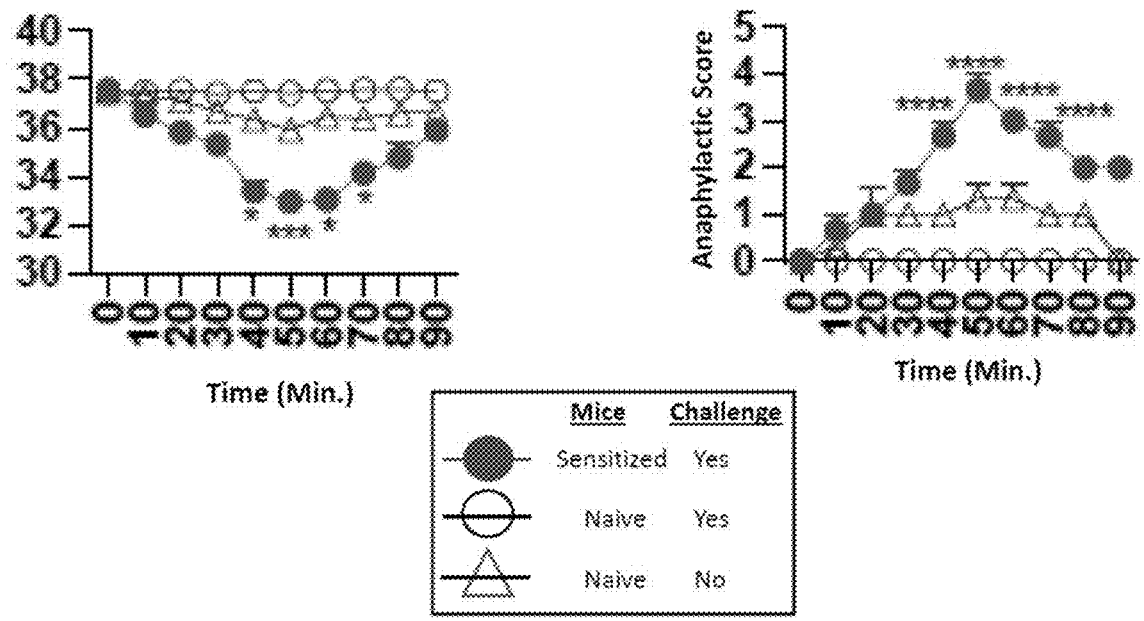
FIG. 8 (left) is a graph showing the body temperature (° C.) as a function of time for naïve and sensitized mouse groups, after oral challenge with PE, as measured with a rectal probe.
Figure 9:
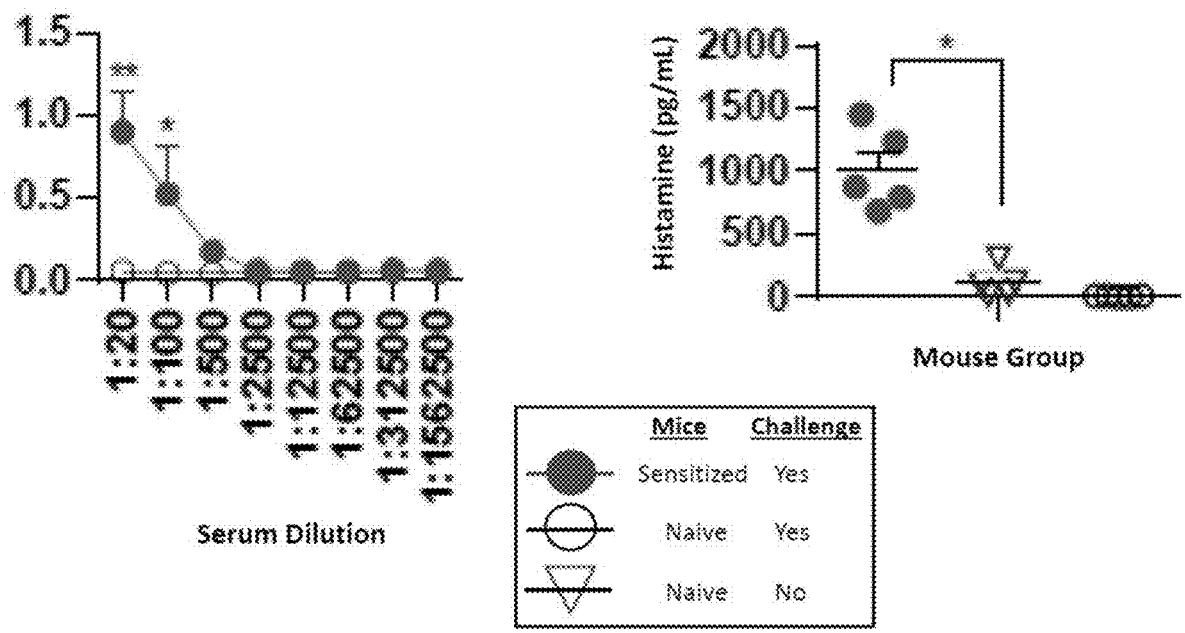
FIG. 9 (left) is a graph of PE-specific IgE antibodies in naïve and sensitized mouse groups after oral challenge with PE.

To assess the therapeutic efficacy of peanut extract (PE) coated microneedles, a mouse peanut allergy model was established. Using a previously published protocol (Dioszeghy et al. (2014). Clin. Exp. Allergy 44(6): pp. 867-881, incorporated by reference herein in its entirety for all purposes) mice were sensitized to peanut by oral gavage with 1 mg PE+10 μg cholera toxin (CT) weekly for six weeks (FIG. 7). To check if mice were successfully made allergic to PE, the mice were challenged orally with 20 mg PE (10 mg+10 mg at 30 min interval), and body temperature and clinical scores were recorded. Significant drop (p<0.0001) in body temperature (FIG. 8, left) and significantly higher anaphylactic score (FIG. 8, right) in sensitized mice in comparison to control naïve mice verified the progression of allergic reaction in sensitized mice. Five minutes post challenge, blood was also collected to analyze anti-PE IgE antibodies and histamine, which is released by mast cells and basophils during an allergic reaction. An elevated level of anti-PE IgE (FIG. 9, left) and histamine (FIG. 9, right) further verified successful development of the mouse peanut allergy model.

Example 3—Generation of Peanut Extract Specific Antibodies

Figure 10:
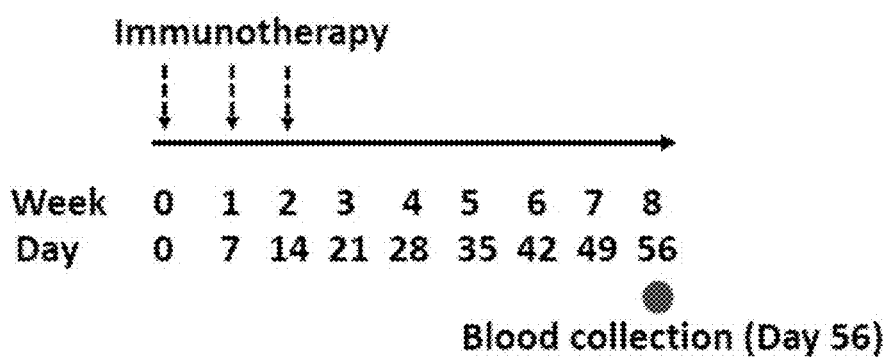
FIG. 10 is an immunotherapy schedule employed with peanut coated microneedles. Schedule shows the effect of PE dose on immune response after vaccination with PE coated MNs. Microneedles coated with 1, 5 or 25 µg PE were used at one dose per week. Six weeks later (at day 56), mice were bled to check for anti-PE responses.
Figure 11:
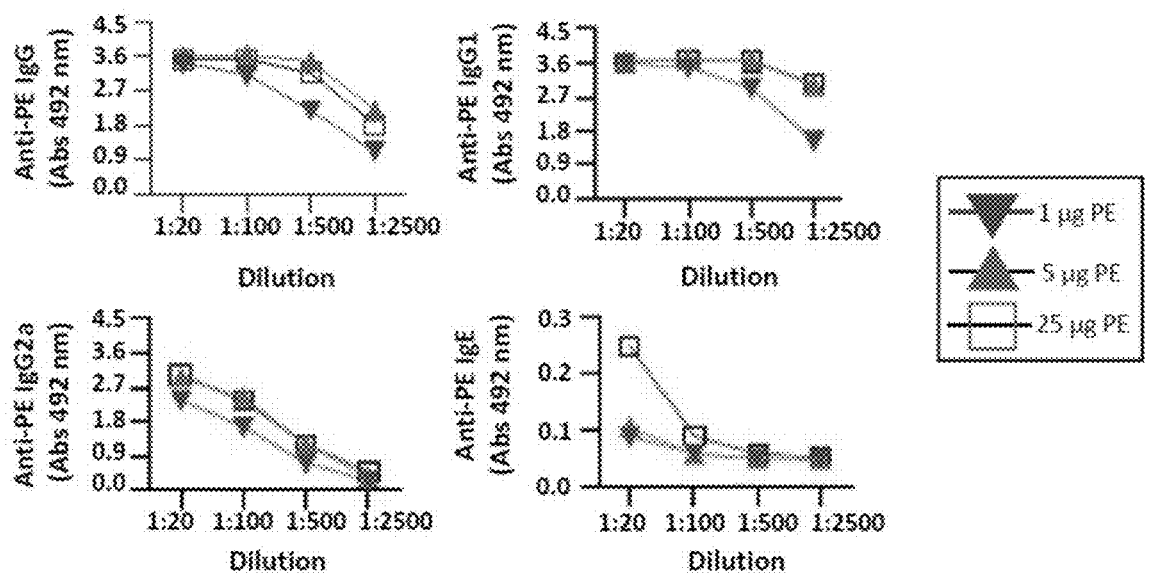
FIG. 11 (top left) is a graph of anti-PE IgG antibodies, as measured by ELISA at different serum dilutions.

To determine the ability of peanut extract (PE) coated microneedles to generate an immune response, microneedles coated with 1, 5 or 25 µg PE were used to immunize naïve mice three times (one dose per week) (FIG. 10). Six weeks later (at day 56), mice were bled to check for anti-PE responses. The mice were then euthanized and their bone marrows and spleens were aseptically collected. All three PE doses were able to induce PE-specific IgG, IgG1 and IgG2a antibodies (FIG. 11). The 5 µg and 25 µg PE doses had similar antibody levels, while the 1 µg PE dose induced slightly lower anti-PE antibodies, although the difference was not statistically significant ($p > 0.05$).

Figure 12:
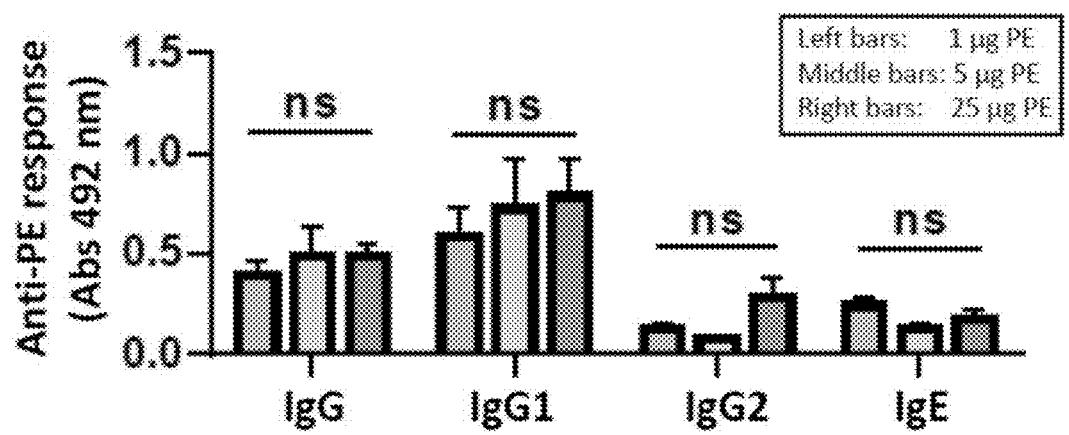
FIG. 12 is a bar graph showing PE specific antibody response for the three microneedle groups. At day 56, mice were euthanized and bone marrow was aseptically collected. Bone marrow cells were cultured in RPMI medium containing penicillin-streptomycin and 10% FBS. After 72 hr., supernatant was collected to analyze PE specific antibodies using ELISA. Data illustrated as mean±SEM; ns: not significant.

The antibody response from peripheral B cells of the bone marrow cells was also evaluated. All IgG subtypes and IgE were detectable in supernatant of bone marrow cultures irrespective of the dose (FIG. 12). Low anti-P E IgE responses are indicative that microneedle-based allergen immunotherapy does not cause sensitization to peanut. Without wishing to be bound by theory, it is thought that the ability to detect antibody secretion in the bone marrow offers the possibility that long-term plasma cells that secrete anti-PE antibodies might be stimulated, which might imply the ability to generate long term sustained unresponsiveness to peanut allergen through microneedle based peanut immunotherapy.

Example 4—Assessment of Immune Response

Figure 13:
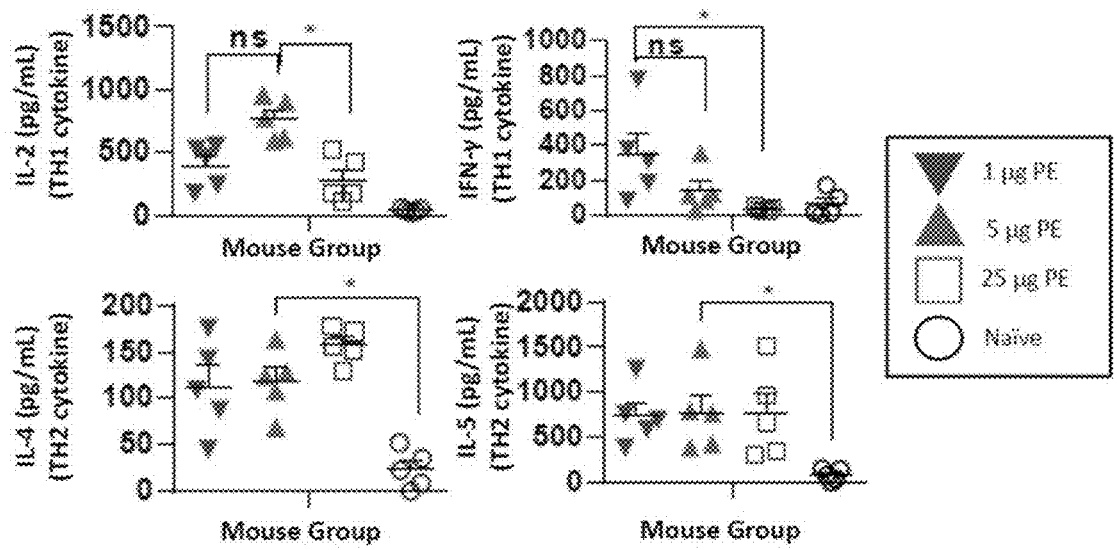
FIG. 13 are graphs showing cytokine response of mice after splenocyte restimulation (IL-2, top left; IFN-$\gamma$, top right; IL-4, bottom left; IL-5, bottom right). At day 56, mice were euthanized and spleen was aseptically collected. Splenocytes were restimulated with PE (200 µg/ml) in an in vitro culture. After 12 hr. of restimulation, supernatant was collected to analyze IL-2, while other cytokines were analyzed after 72 hr. of restimulation. All data are illustrated as mean±SEM. *$p<0.05$, and ns: not significant.

To assess the nature of immune response (Th1 vs Th2) induced by PE-coated microneedles, splenocytes (from spleens as collected in Example 3, above) were cultured in vitro, and re-stimulated with PE (200 µg/ml). After 72 hr. of re-stimulation, supernatants were collected to analyze the secreted cytokines. Both Th1 (IL-2 & IFN-γ) and Th2 cytokines (IL-4 & IL-5) were secreted irrespective of PE dose. Expression of IL-2 was higher in 5 µg PE group than the 25 µg PE, while IFN-γ was observed higher in 1 µg PE group (FIG. 13). There was no considerable difference observed in IL-4 and IL-5 expression between the 1, 5, and 25 µg PE doses. Microneedles thus appear to induce a mixed Th1/Th2 response.

Example 5—Assessment of Anaphylactic Shock in Peanut Sensitized Mice

Figure 14:
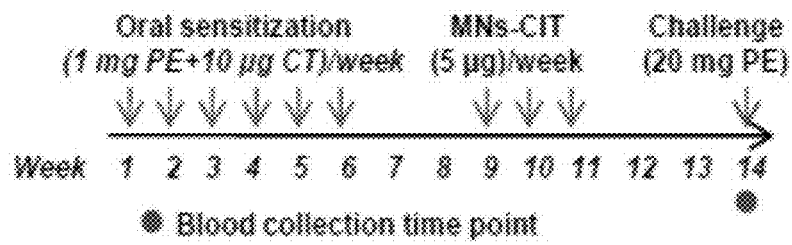
FIG. 14 is a microneedle immunotherapy schedule. Mice were sensitized orally to peanut and treated with 5 µg PE coated on microneedles (MNs)-CIT (cutaneous immunotherapy) every week. Three weeks post-immunotherapy, mice were challenged orally with high dose of PE (20 mg: 10 mg+10 mg at 30 min interval).

In this experiment, it was determined whether peanut extract (PE) coated microneedles provide a therapeutic effect in peanut sensitized (allergic) mice. The experimental protocol is shown in FIG. 14. First, mice were sensitized to peanut as described above in Example 2. Then, after a rest of three weeks, the microneedle cutaneous immunotherapy (CIT) group received 5 µg PE coated on microneedles every week for a total of three weeks. After a rest of three more weeks, mice were challenged orally with a high dose of PE (20 mg/mouse: 10 mg+10 mg delivered at 30 min interval via oral gavage) (FIG. 14).

Figure 15:
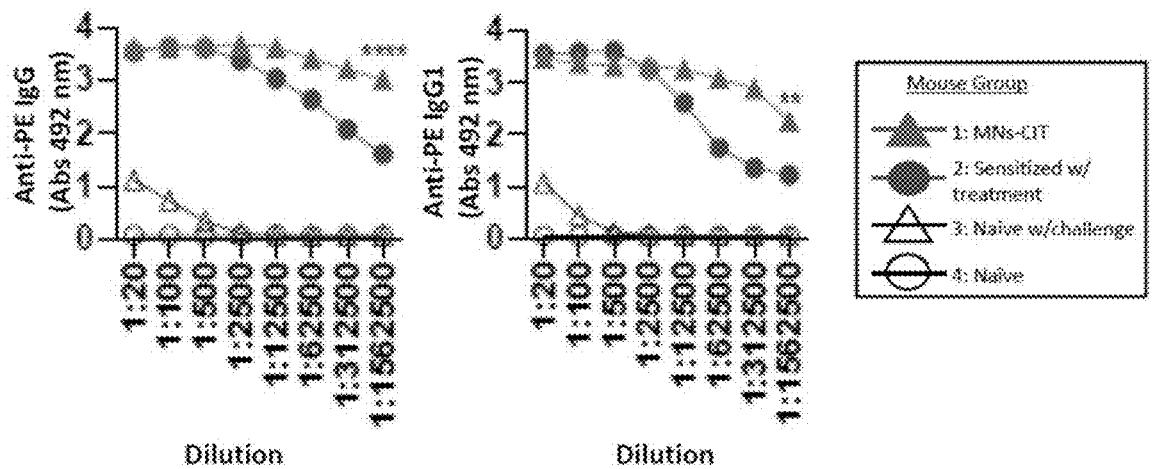
FIG. 15 are graphs of anti PE antibodies in plasma (at different dilutions) after oral challenge. IgG—left graph. IgG1—right graph. Plasma was collected 5 minutes post challenge.
Figure 16:
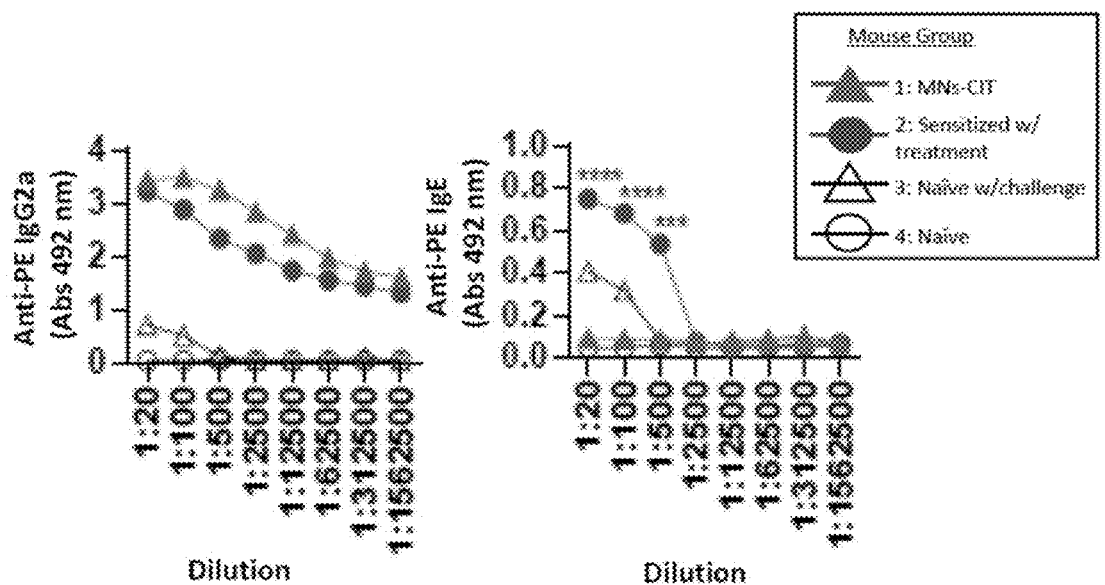
FIG. 16 are graphs of anti PE antibodies in plasma (at different dilutions) after oral challenge. IgG2a—left graph. IgE—right graph. Plasma was collected 5 minutes post challenge.
Figure 17:
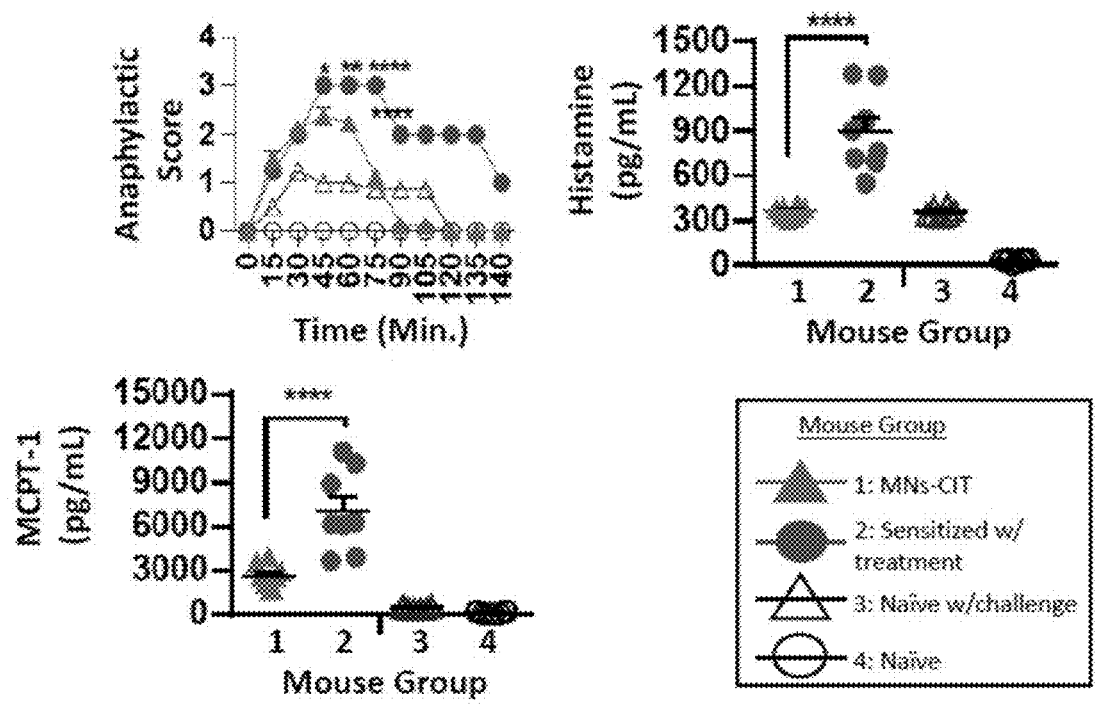
FIG. 17 are graphs showing various anaphylactic indicators for mouse treatment groups (after oral challenge with peanut extract (PE)).

The following control groups were included: (i) peanut sensitized mice that did not receive microneedle-CIT treatment but received oral PE challenge, (ii) naïve mice that received oral PE challenge, and (iii) naïve mice without treatment or oral challenge. For all groups, five minutes after oral PE challenge, mice were bled to collect plasma for analysis of inflammatory markers. Mice were monitored every 10 min. to assess the severity of anaphylaxis based on a scoring system described previously (see, McCaskill et al. (1984). Immunology 51(4), pp. 669-77, incorporated herein by reference in its entirety for all purposes), and for change in body temperature measured with a rectal probe. The microneedle-CIT group had higher anti-PE IgG, IgG1 and IgG2a in plasma as compared to the allergic/sensitized but untreated group (FIGS. 15 and 16). Anti-PE IgE levels were significantly lower in the microneedle-CIT group as compared to the untreated group. Moreover, lower score of anaphylaxis, and low expression of histamine and mast cell protease-1 (MCPT-1) in plasma of mice that were treated with microneedle-CIT as compared to untreated group further demonstrated the therapeutic efficacy of microneedle-CIT (FIG. 17). No considerable differences were observed in change of body temperature between the different groups.

Example 6—Peanut Allergen Dose Titration

Naïve mice will be given 0.1 µg, 0.3 µg, 0.6 µg, 1 µg, 2 µg, or 5 µg peanut allergen, in the form of peanut extract (PE) coated on microneedles, once a week for 12 weeks. Blood will be collected every two weeks to measure anti-PE antibodies set forth in FIG. 11 and the corresponding Example. At the end of the 12-week period, mice will be euthanized, and bone marrow and spleen will be collected to analyze antibody secreting cells in bone marrow, and cytokines from splenocyte restimulation (e.g., the antibodies set forth in FIG. 11 and the cytokines set forth in FIG. 13, and the corresponding Examples). Sham (microneedles coated with excipients but no PE) and naïve groups will be included as controls.

Example 7—Comparison of Microneedle Lengths

The immune response generated from microneedles (MNs) of various lengths (e.g., 200 µm, 300 µm, 400, µm, 500 µm, 600 µm and 700 µm will be assessed.

The delivery efficiency from MNs of different lengths will be evaluated as by coating MNs with fluorescent Ova and measuring the fluorescence delivered via the microneedles (see, e.g., FIG. 6).

Immune response will be characterized by measuring the antibodies and/or cytokines described previously in FIGS. 11 and 13 and the corresponding Examples.

Example 8—Comparison of Allergen Delivery with and without Adjuvant

Figure 18:
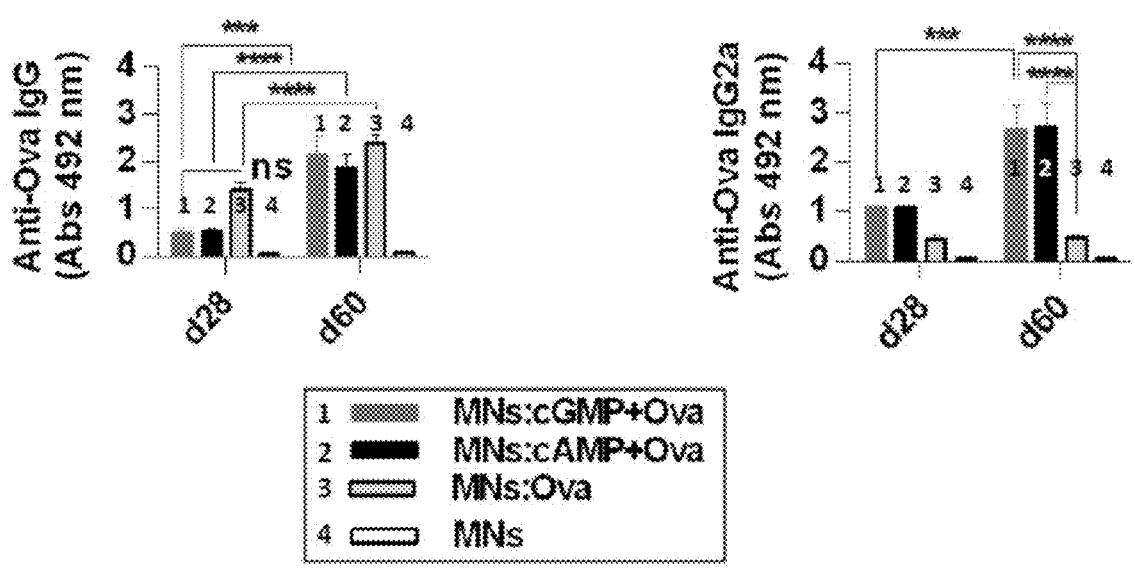
FIG. 18 are graphs for anti-ovalbumin (Ova) response in mice treated with Ova coated MNs with or without stimulator of interferon genes (STING) ligand adjuvants. Mice were treated at day (d) 0 and d28 with Ova (25 µg) with or without STING adjuvants cGMP (25 µg) or cAMP (25 µg) using coated MNs. Serum was collected on d28 and d60 to determine anti-Ova antibody response using the ELISA method.

The effect of cGMP and cAMP, which are ligands of Stimulator of Interferon Genes (STING) (also known as transmembrane protein 173 (TMEM173)) was evaluated (FIG. 18). cGMP and cAMP were added to coated microneedle formulation containing ovalbumin as a model allergen. FIG. 18 shows an increased Th1 response (higher IgG2a) for the compositions containing the STING ligands, as compared to ovalbumin composition alone.

Figure 19:
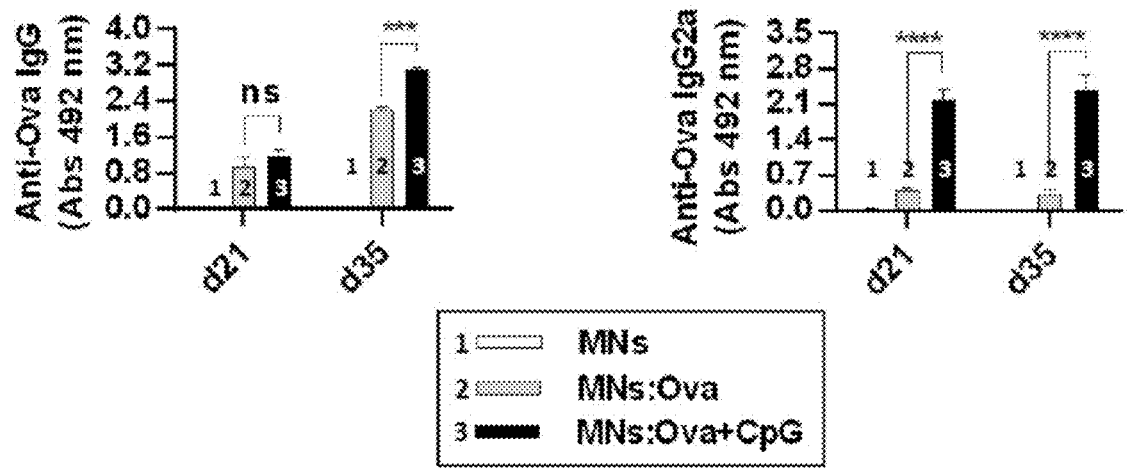
FIG. 19 are graphs for anti-Ova response in mice treated with Ova coated MNs with or without CpG adjuvant. Mice were treated on day (d) 0, d7, d14 with Ova (25 µg)±CpG (25 µg) and bled at d21 and d35 to determine anti-Ova antibody response using the ELISA method.

The effect of CpG as an adjuvant was evaluated on IgG response (FIG. 19). CpG (#1826, a mouse specific CpG, 5'-tccatgacgttcctgacgtt-3': 20 nucleotides with bases having phosphorothioate bonds to make it nuclease resistant) was added to microneedle coating compositions containing ovalbumin as a model allergen. Addition of CpG adjuvant increased total IgG and IgG2a (Th1 type response) as compared to ovalbumin without CpG as adjuvant (FIG. 19).

Figure 20:
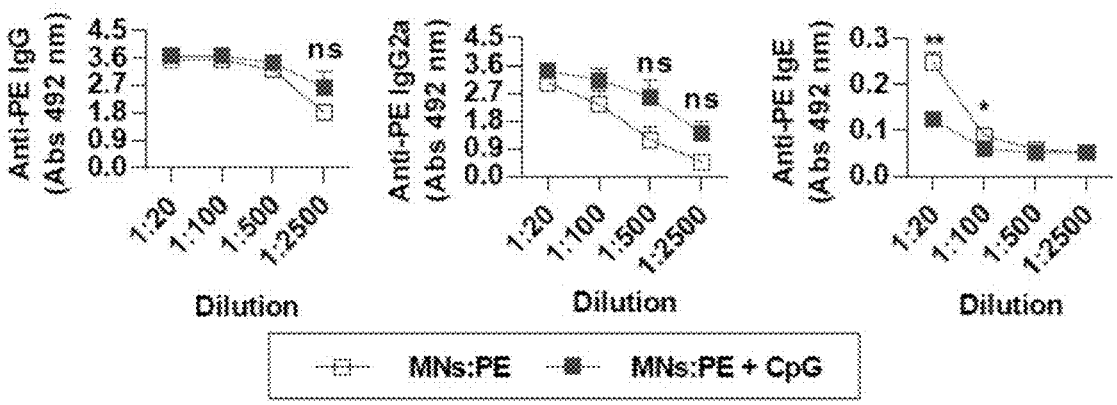
FIG. 20 are graphs for anti-peanut extract (PE) response in mice treated with PE coated MNs with or without CpG adjuvant. Mice were treated on day (d) 0, d7, and d14 with PE (25 µg)±CpG adjuvant (25 µg) coated on MNs. Serum was collected on d56 to determine anti-Ova antibody response with ELISA method.
Figure 21:
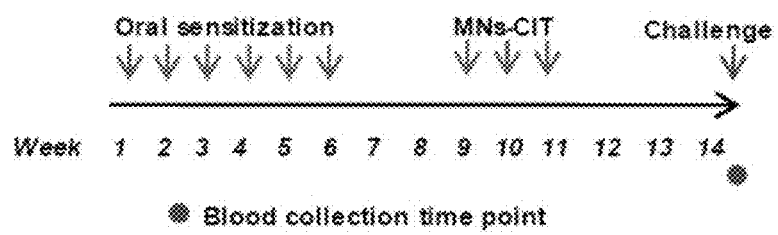
FIG. 21 shows a peanut allergy immunotherapeutic schedule for examining effect of adjuvant. Immunotherapy schedule; mice were sensitized orally every week up to six weeks with 1 mg peanut extract (PE)+10 µg cholera toxin (CT). Three weeks later, sensitized mice were treated with MNs coated with PE (5 µg)±CpG (5 µg). Four weeks post-immunotherapy, mice were challenged orally with a high dose of PE (20 mg).
Figure 22:
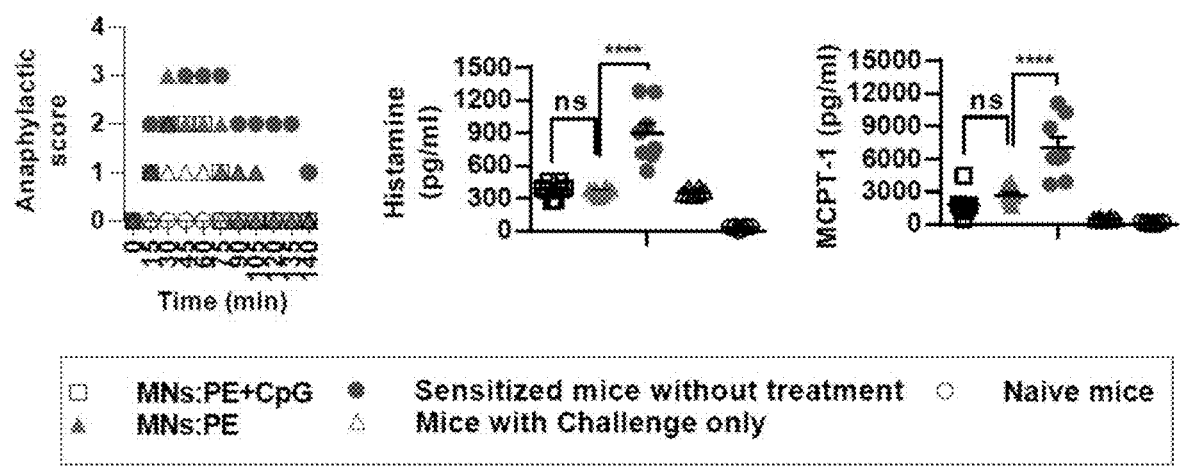
FIG. 22 shows therapeutic efficacy of CpG adjuvant in peanut allergy treatment. Five minutes after oral peanut challenge, mice were assessed for allergic reaction.

The effect of CpG was assessed with peanut extract as the allergen. Results are shown in FIG. 20. When CpG (25 µg) was included in compositions containing 25 µg peanut extract and coated on microneedles, there was some increase in total IgG and IgG2a as compared to compositions containing PE without CpG. Further, CpG significantly reduced anti-peanut IgE levels (FIG. 20).

Addition of adjuvants in MN coating compositions for the treatment of peanut allergy was tested. The schedule set forth in FIG. 21 was followed. Mice were sensitized to peanut. Allergic mice were treated with either peanut extract (PE) or peanut extract+CpG (PE+CpG), and subsequently, mice were orally challenged with peanut to test the treatment efficacy. None of the mice in PE+CpG group (0/8) had an anaphylactic score of greater than 2 while in the PE group (no CpG usage) 3/8 mice had a score>3 (FIG. 22). The anaphylactic score is a measure of severity of the anaphylactic reaction with lower score indicating a less severe reaction.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least 1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

The invention claimed is:

1. A method for treating a peanut allergy in a subject sensitized to the peanut allergen and in need thereof, comprising,
delivering an effective amount of the peanut allergen into the subject's cutis skin layer, wherein the delivering step is carried out once daily during an administration period, and the delivering comprises,
(i) inserting one or more solid microneedles each comprising a base, shaft and tip into the subject's skin, wherein at least one microneedle of the one or more solid microneedles does not extend beyond the cutis once inserted, and is coated with the peanut allergen; and
(ii) allowing the peanut allergen to dissociate from the one or more solid microneedles while inserted in the subject's cutis; and
(iii) removing the one or more solid microneedles from the subject's skin.

2. The method of claim 1, wherein the one or more solid microneedles extends from an adhesive substrate.

3. The method of claim 1, wherein the one or more solid microneedles is stainless steel.

4. The method of claim 1, wherein the one or more solid microneedles is present in a microneedle array extending from a common substrate.

5. The method of claim 1, wherein the average width of the one or more solid microneedles, as measured at the widest cross section of each respective microneedle of the one or more solid microneedles, is from about 20 μm to about 500 μm, or from about 50 μm to about 350 μm, or from about 100 μm to about 250 μm.

6. The method of claim 1, wherein the one or more microneedles comprises a plurality of microneedles, and substantially all the microneedles of the plurality are coated with the peanut allergen.

7. The method of claim 1, wherein the one or more microneedles comprises from about 10 to about 200 microneedles.

8. The method of claim 1, wherein the peanut allergen comprises Ara h1, Ara h2, Ara h3, Ara h4, Ara h5, Ara h6, Ara h7, Ara h8, Ara h9, Ara h10, Ara h11, Ara h12, Ara h13, a peptide fragment thereof, or a combination thereof.

9. The method of claim 1, wherein the one or more solid microneedles is coated with an adjuvant.

10. The method of claim 1, wherein each microneedle of the one or more microneedles does not extend beyond the epidermis skin layer.

11. The method of claim 1, wherein each microneedle of the one or more microneedles does not extend beyond the dermis skin layer.

12. The method of claim 1, wherein at least about 40% of the allergen disassociates from the at least one microneedle while inserted in the subject's cutis.

13. The method of claim 1, wherein the peanut allergen dissociates from the at least one microneedle for about 1 minute to about 10 minutes.

14. The method of claim 1, wherein the delivering an effective amount of the peanut allergen comprises delivering substantially the same dose of the peanut allergen during the administration period.

15. The method of claim 1, wherein delivering an effective amount of the peanut allergen comprises delivering an escalating dosage of the peanut allergen at least once during the administration period.

16. The method of claim 1, wherein delivering an effective amount of the peanut allergen comprises delivering an escalating dosage of the peanut allergen at least twice during the administration period.

17. The method of claim 1, wherein delivering an effective amount of the peanut allergen comprises delivering an escalating dosage of the peanut allergen at least three times during the administration period.

18. The method of claim 1, wherein the treating comprises desensitizing the subject to the peanut allergen.

19. The method of claim 1, wherein treating comprises decreasing the number of peanut allergen specific IgE antibodies in the subject, as compared to the number of peanut allergen specific IgE antibodies secreted by the subject prior to the treating.

20. The method of claim 1, wherein treating comprises increasing the number of peanut allergen specific IgG antibodies in the subject, as compared to the number of peanut allergen specific IgG antibodies secreted prior to the treating.

21. The method of claim 9, wherein the adjuvant comprises CpG oligonucleotide.

22. The method of claim 9, wherein the adjuvant comprises monophosphoryl lipid A (MPL-A).

23. The method of claim 9, wherein the adjuvant comprises a stimulator of interferon genes (STING) ligand.

24. The method of claim 9, wherein the adjuvant comprises L-Tyrosine.

25. The method of claim 9, wherein the adjuvant comprises L-Tyrosine in combination with MPL-A.

26. The method of claim 8, wherein the peanut allergen comprises Ara h1, Ara h2, Ara h6, a peptide fragment thereof, or a combination thereof.

27. The method of claim 4, wherein the microneedle array comprises from about 10 to about 500 microneedles.

28. The method of claim 27, wherein the microneedle array comprises from about 20 to about 150 microneedles.

29. The method of claim 4, wherein the average length of microneedles in the microneedle array is from about 500 μm to about 1000 μm.

30. The method of claim 4, wherein the average length of microneedles in the microneedle array is from about 200 μm to about 900 μm.

* * * * *

SEQUENCE LISTING

<160> NUMBER OF SEQ ID NOS: 29

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Pro Gly Gln Phe Glu Asp Phe Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Tyr Leu Gln Gly Phe Ser Arg Asn
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Phe Asn Ala Glu Phe Asn Glu Ile Arg Arg
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Gln Glu Glu Arg Gly Gln Arg Arg
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Asp Ile Thr Asn Pro Ile Asn Leu Arg Glu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Asn Asn Phe Gly Lys Leu Phe Glu Val Lys
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Gly Asn Leu Glu Leu Val
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Arg Arg Tyr Thr Ala Arg Leu Lys Glu Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Glu Leu His Leu Leu Gly Phe Gly Ile Asn
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

His Arg Ile Phe Leu Ala Gly Asp Lys Asp
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Ile Asp Gln Ile Glu Lys Gln Ala Lys Asp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Lys Asp Leu Ala Phe Pro Gly Ser Gly Glu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Lys Glu Ser His Phe Val Ser Ala Arg Pro
1               5                   10

<210> SEQ ID NO 14
<211> LENGTH: 25
<212> TYPE: PRT
<213> ORGANISM: Artificial Sequence
<220> FEATURE:
<223> OTHER INFORMATION: Synthetic peptide

<400> SEQUENCE: 14

Asn Glu Gly Val Ile Val Lys Val Ser Lys Glu His Val Glu Leu
1               5                   10                  15

Thr Lys His Ala Lys Ser Val Ser Lys
            20                  25

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

His Ala Ser Ala Arg Gln Gln Trp Glu Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Gln Trp Glu Leu Gln Gly Asp Arg Arg Cys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Asp Arg Arg Cys Gln Ser Gln Leu Glu Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Leu Arg Pro Cys Glu Gln His Leu Met Gln

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Lys Ile Gln Arg Asp Glu Asp Ser Tyr Glu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Tyr Glu Arg Asp Pro Tyr Ser Pro Ser Gln
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Ser Gln Asp Pro Tyr Ser Pro Ser Pro Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

Asp Arg Leu Gln Gly Arg Gln Gln Glu Gln
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Lys Arg Glu Leu Arg Asn Leu Pro Gln Gln
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Gln Arg Cys Asp Leu Asp Val Glu Ser Gly
1               5                   10

```
<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Ile Glu Thr Trp Asn Pro Asn Asn Gln Glu Phe Glu Cys Ala Gly
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

Gly Asn Ile Phe Ser Gly Phe Thr Pro Glu Phe Leu Ala Gln Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Val Thr Val Arg Gly Gly Leu Arg Ile Leu Ser Pro Asp Arg Lys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

Asp Glu Asp Glu Tyr Glu Tyr Asp Glu Glu Asp Arg Arg Arg Gly
1               5                   10                  15

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
tccatgacgt tcctgacgtt                                           20
```